(12) United States Patent
Antharavally et al.

(10) Patent No.: US 8,507,291 B1
(45) Date of Patent: Aug. 13, 2013

(54) DETERGENT REMOVAL FROM PROTEIN SAMPLES PRIOR TO MASS SPECTROMETRY ANALYSIS

(75) Inventors: Babu S. Antharavally, Caledonia, IL (US); A. Krishna Mallia, Rockford, IL (US); Ashok Salunkhe, Rockton, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 309 days.

(21) Appl. No.: 12/782,430

(22) Filed: May 18, 2010

Related U.S. Application Data

(60) Provisional application No. 61/181,921, filed on May 28, 2009.

(51) Int. Cl.
*G01N 1/00* (2006.01)
*G01N 1/18* (2006.01)

(52) U.S. Cl.
USPC .......................................... 436/175; 436/178

(58) Field of Classification Search
USPC ................................. 436/175, 178
See application file for complete search history.

(56) References Cited

U.S. PATENT DOCUMENTS 5,360,899 A * 11/1994 Nussstein et al. ............. 536/4.1

OTHER PUBLICATIONS

Brewster et al. Stabilization of Aspartmame by Cyclodextrins; International Journal of Pharmaceutics, vol. 75 (1991) pp. R5-R8.*
DeGrip et al. Selective Detergent-Extraction From Mixed Detergent/Lipid/Protein Micelles, Using Cyclodextrin Inclusion Compounds: A Novel Generic Approach for the Preparation of Proteoliposomes; Biochemical Journal, vol. 330 (1998) pp. 667-674.*
Mannen et al. Expanded-Bed Protein Refolding Using a Solid-Phase Artificial Chaperone; Journal of Bioscience and Bioengineering, vol. 91, No. 4 (2001) pp. 403-408.*
Manza et al. Sample Preparation and Digestion for Proteomic Analysis Using Spin Filters; Proteomics, vol. 5 (2005) pp. 1742-1745.*
Ogino et al. Membrane Binding Properties and Terminal Residues of the Mature Hepatitis C Virus Capsid Protein in Insect Cells; Journal of Virology, vol. 78, No. 21 (2004) pp. 11766-11777.*
Gaylor et al. Removal of Nonionic Detergents From Proteins by Chromatography on Sephadex LH-20; Analytical Biochemistry, vol. 28 (1969) pp. 361-368.*
Hjelmeland, L.M., Removal of Detergents from Membrane Proteins, Methods in Enzymology 182, 277-282 (1990).
Arnold T. and Linke, D., Phase separation in the isolation and purification of membrane proteins, Biotechniques 43, 427-440 (2007).
Li, J.J., et al., Immobilized beta-cyclodextrin polymer couples to agarose gel properly refolding recombinan *Staphylococcus aureus* elongation factor-G in comgination with detergent micelle, Protein Expr. Purif. 45, 72-79 (2006).

\* cited by examiner

*Primary Examiner* — Susan Hanley
*Assistant Examiner* — Paul Martin
(74) *Attorney, Agent, or Firm* — Thompson Hine LLP

(57) ABSTRACT

A method to remove detergents from a biological protein sample that is to be analyzed by mass spectroscopy (MS). The method uses a high performance cyclodextrin polymer resin to remove detergents, which interfere with MS analysis, from a sample containing proteins, peptides, amino acids, etc.

9 Claims, 26 Drawing Sheets

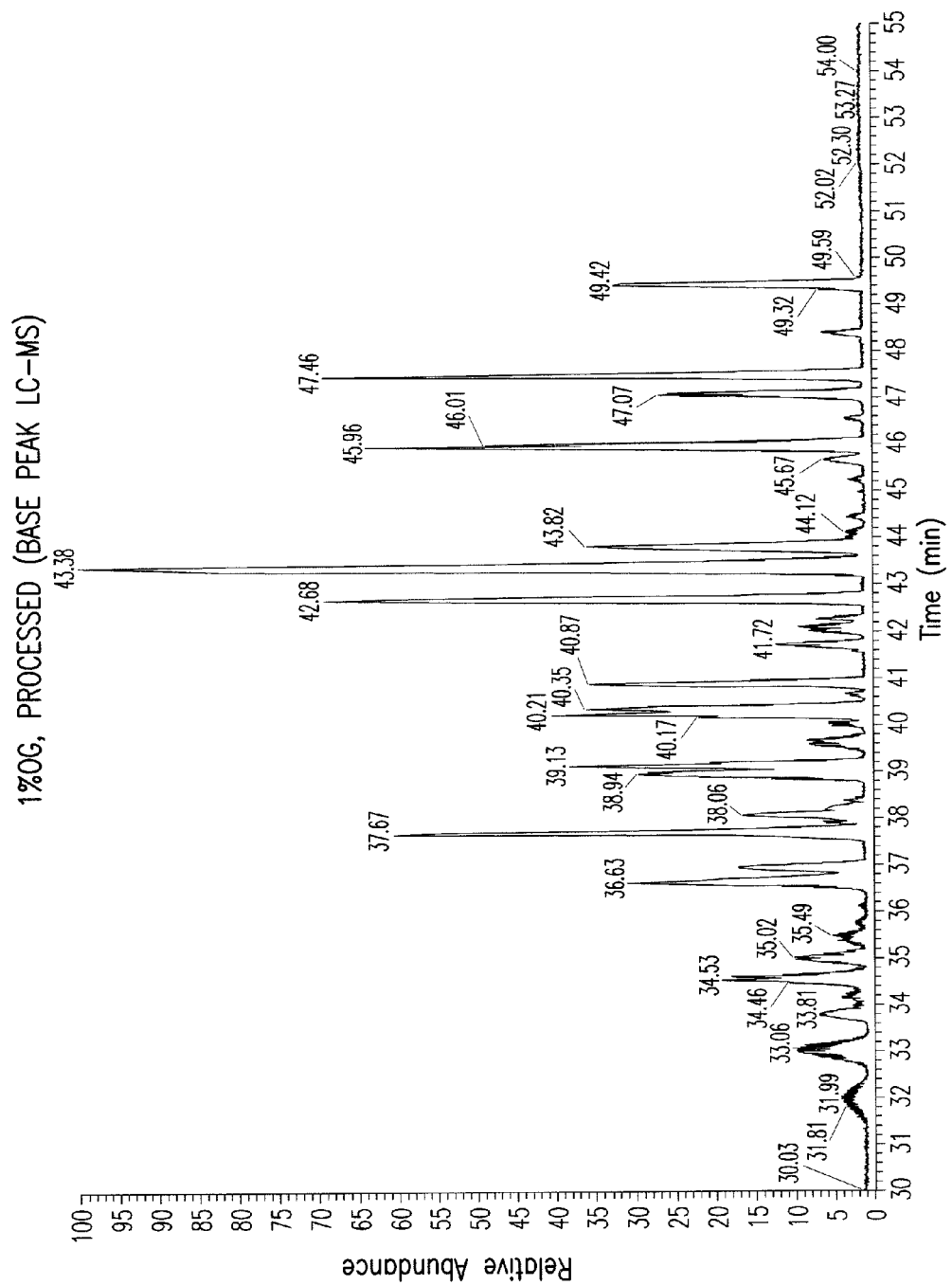

DETERGENT REMOVAL FROM PROTEIN SAMPLES PRIOR TO MASS SPECTROMETRY ANALYSIS

This application claims priority from U.S. Patent Application Ser. No. 61/181,921 filed May 28, 2009 and incorporated by reference herein in its entirety.

In preparing biological samples for laboratory analysis, detergents solubilize proteins, stabilize proteins, and disaggregate protein complexes that may be present in the sample. Membrane-bound proteins, in particular, frequently require detergent treatment for solubilization.

The presence of excess unbound detergent in the biological sample interferes with many downstream applications, such as enzyme-linked immunosorbent assays (ELISA), isoelectric focusing, and mass spectrometry (MS). Thus, there is a need to remove detergents from biological samples to be used in downstream applications. Detergents must be removed from biological samples that will undergo MS for sensitive detection of peptides because detergents usually form adducts with peptides and/or proteins. Adducts may shift m/z values, and the presence of detergents produces erratic (noisy) baseline levels. Detergents must be removed from a biological sample to avoid ion source fouling, and hence the need to clean the ion source, which results in substantial time that the mass spectrometer cannot be used (down time). Detergents must be removed from a biological sample prior to MS analysis to facilitate the identification of target proteins, to overcome suppression of ionization in Matrix-Assisted Laser Desorption Ionization MS (MALDI MS) and electrospray ionization MS (ESI-MS), to overcome interference with binding, elution, ionization, to overcome poor chromatographic resolution of proteins and peptides in liquid chromatography-MS (LC-MS), to overcome low signal-to-noise ratio, and to overcome formation and domination of ion signals from detergent clusters, e.g., in LC-MS/MS and MALDI-MS data.

Methods to remove detergents from biological samples include hydrophobic interaction chromatography, size exclusion chromatography, ion-exchange chromatography, and dialysis. These methods are tedious, labor intensive, and can result in significant sample loss.

The inventive method uses a high performance resin to remove detergents from a biological sample that is to be analyzed by MS. In one embodiment, the sample contains or is capable of containing proteins, peptides, and/or amino acids, either in the presence or absence of post-translational modifications (e.g., glycosylation, phosphorylation, etc), either in the presence or absence of synthetic modifications (e.g., by mass tags, isotopic tags from incubation such as in stable isotope labeling with amino acids in cell culture (SILAC)), and using samples in which peptides are derived from multiple samples (e.g., SILAC experiments, mass tag experiments). All such compounds may be collectively referred to as proteins.

Detergents are defined as surfactants that are distinguished by their amphiphilic structure. Each molecule contains both hydrophilic and hydrophobic moieties, which gives rise to the phenomenon of surface activity. Detergents form micelles and are thus significantly soluble in water. Detergents are most commonly classified on the basis of the charge and/or nature of the hydrophilic portion (head group), and the flexibility and/or chemical nature of the hydrophobic portion. Head groups may be anionic, zwitterionic, nonionic, or cationic. Anionic head groups are negatively charged moieties such as carboxylate, sulfate, or sulfonate. Zwitterionic head groups contain both a negatively charged moiety and a positively charged moiety. Most zwitterionic detergents are effectively neutral. Nonionic head groups contain no charged moieties. Detergents with cationic head groups are usually quaternary ammonium compounds. Examples of detergents include, but are not limited to, CHAPS (bile-salt based zwitterionic), Brij-35 (polyoxyethylene glycol monoether, nonionic), lauryl maltoside (LM, glycosidic non-ionic), octyl glucoside (OG, glycosidic non-ionic), octyl thioglucoside (OTG, glycosidic non-ionic), sodium deoxycholate (SDC, ionic), sodium dodecyl sulfate (SDS, ionic), TRITON® X-100 (tertiary-octylphenol poly (ethyleneglycolether) based non-ionic), TRITON® X-114 (tertiary-octylphenol poly (ethyleneglycolether) based non-ionic), and NP-40 (tertiary-octylphenol poly (ethyleneglycolether) based non-ionic). Examples of detergents that interfere with in LC-MS/MS are CHAPS, LM, OG, OTG, TRITON® X-100, TRITON® X-114, NP-40, Tween-20, SDC, and SDS. Examples of detergents that interfere with MALDI-MS are CHAPS, LM, OG, OTG, TRITON® X-100, TRITON® X-114, Tween-20, NP-40, SDS, and SDC.

One or more detergents may have been introduced into the biological sample for various reasons. As one example, a detergent may be introduced in order to recover the protein from tissues, cells, membranes, membrane fractions, and/or another biological source. As one example, a detergent may be introduced to separate the protein from other biomolecules, and/or to separate protein subunits. In one embodiment, the same or different detergents may be introduced before or during digestion of the protein or of the subunits into peptides. In one embodiment, digestion preserves post-translational modifications, e.g., phosphate. In one embodiment, protein separation (e.g., by electrophoresis, ion-chromatography, etc.) may have occurred before or after a digestion step, and before or after a detergent removal step.

The described method removes such detergents.

In one embodiment, cyclodextrin is polymerized by crosslinking. In one embodiment, cyclodextrin is polymerized using a bi-functional cross linking reagent, e.g., epichlorohydrin, diepoxide, etc. In one embodiment, cyclodextrin is polymerized according to U.S. Pat. No. 5,360,899, which is expressly incorporated by reference in its entirety. In one embodiment, the cyclodextrin polymer is (2-hydroxyethyl)-β-cyclodextrin (HEBC) polymer, commercially available as Thermo Fisher Detergent Removing Resin®. HEBC polymer has a high cyclodextrin content and possesses good mechanical properties. In one embodiment, the HEBC polymer size ranges from about 45 µm to about 250 µm. Polymers formed from α-, β-, and γ-cyclodextrin, and their derivatives, also bind detergents. Thus, polymers formed from other cyclodextrins are also suitable.

In one embodiment, HEBC was immobilized to a support matrix, e.g., agarose beads. In one embodiment, HEBC was not immobilized to a support matrix, but instead was polymerized to synthesize a resin bead.

Figure 1:
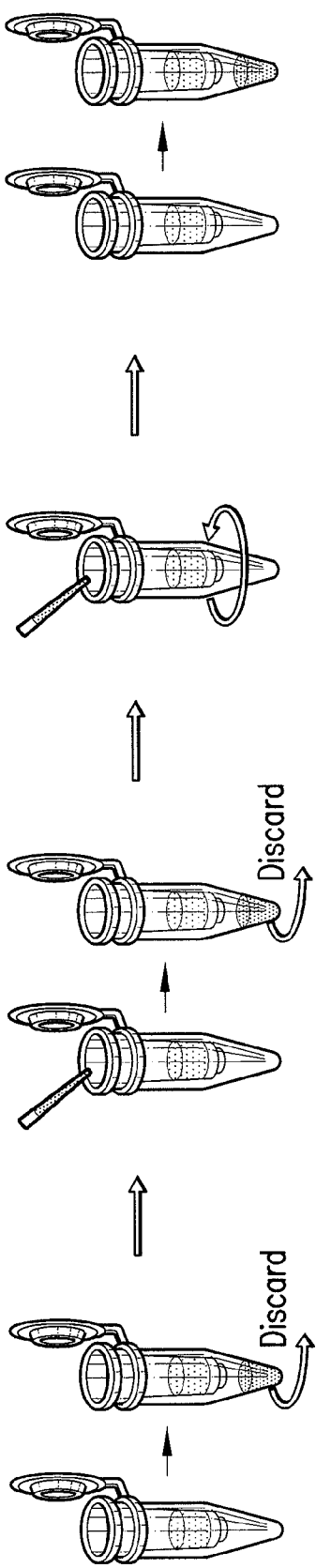
FIG. 1 shows a schematic representation of one embodiment of the method.

FIG. 1 schematically shows one embodiment of the method. The resin was prepared by removing storage buffer (e.g., by centrifugation). In one embodiment, a spin column containing storage buffer is centrifuged at 1,500×g for one minute to remove storage buffer. Equilibration buffer was then added to the resin, the composition was centrifuged, and the equilibration buffer was discarded. In one embodiment, 0.4 ml of equilibration buffer is added to a spin column and centrifuged at 1,500×g for one minute, with the flow-through being discarded. The process was repeated two additional times. The biological sample containing detergent was added to the prepared resin, incubated, and the detergent-free sample was recovered (e.g., by centrifugation). In one embodiment, about 25 µl to about 100 µl of detergent-containing sample is added to the spin column and is allowed to incubate for two minutes at room temperature. The detergent-free sample is then collected after centrifugation at 1,500×g for two minutes. In one embodiment, the method is performed using a spin column. In one embodiment, the method is performed using a gravity flow (drip) column, as known to a person of ordinary skill in the art. In one embodiment, the method is performed using a batch process. In one embodiment, the method is performed at temperatures ranging from about 20° C. to about 25° C. (room temperature). In one embodiment, the method is performed at about 4° C. (cold room temperature). The method can be adapted for use with various sample volumes. For example, HEBC polymer volumes of 125 µl, 0.5 ml, 2 ml and 4 ml have been used to process sample volumes of 25 µl, 100 µl, 500 µl and 2.0 ml, respectively.

The ratio of sample volume to resin volume can range from about 1:1 to about 1:10. In one embodiment, the ratio of sample volume:resin volume is about 1:5.

The method was evaluated using several detergents and using BSA as the protein. A solution of BSA (0.1 ml at a concentration of 1 mg/ml), detergent at the concentrations indicated in Table 1, in 0.15M NaCl, 0.05% sodium azide was processed through 0.5 ml Thermo Scientific Pierce Detergent Removing Resin (Rockford Ill.) as shown in FIG. 1. Residual SDS was measured by a colorimetric method using Stains-All® dye (Sigma-Aldrich). Residual TRITON® X-100, TRITON® X-114 and NP-40 were measured by OD$_{275\ nm}$ with protein absorbance subtracted). Sodium deoxycholate, CHAPS, octyl glucoside, octyl thioglucoside, and lauryl maltoside were measured by a colorimetric method using concentrated sulfuric acid and phenol according to the procedure in Urgani and Warne, Anal. Biochem. 336 (2005) 117. Removal of excess unbound Brij-35 was monitored by LC-MS/MS and MALDI-MS analysis, by visually observing the elimination of the noisy baseline. Protein was determined by the BCA method.

TABLE 1

Table 1 shows the detergent concentrations used in sample preparation and the maximum amount of detergent that can be removed, n = 2.

| Detergent and Maximal Removable Concentration (%) | Detergent Removal (%) | BSA Recovery (%) |
|---|---|---|
| SDS (2.5) | 99 | 95 |
| Sodium Deoxycholate (5) | 99 | 100 |
| CHAPS (3) | 99 | 90 |
| Octyl Glucoside (5) | 99 | 90 |
| Octyl Thioglucoside (5) | 99 | 95 |
| Lauryl Maltoside (1) | 98 | 99 |
| TRITON ® X-100 (2) | 99 | 87 |
| TRITON ® X-114 (2) | 95 | 100 |
| NP-40 (1) | 95 | 91 |
| Brij-35 (1) | 99 | 97 |

The method was evaluated using three detergents and several proteins and a cell lysate. A solution of any of the proteins shown in Table 2 (0.1 ml at a concentration of 1 mg/ml), detergent at the concentrations indicated in Table 2, 0.15M NaCl, and 0.05% sodium azide was processed through 0.5 ml Thermo Scientific Pierce Detergent Removal Resin® as shown in FIG. 1. Residual SDS was measured by a colorimetric method using Stains-All® dye. TRITON® X-100, TRITON® X-114 and NP-40 were measured by OD$_{275\ nm}$ with protein absorbance subtracted. Sodium deoxycholate, CHAPS, octyl glucoside, octyl thioglucoside, and lauryl maltoside were measured by a colorimetric method using concentrated sulfuric acid and phenol as described above. Removal of Brij-35 was monitored by LC-MS/MS and MALDI-MS analysis. Protein was determined by the BCA method.

Table 2 shows the efficiency of detergent removal and recovery of three proteins and one cell lysate. N=2, ND=not determined.

TABLE 2

| | SDS | | TRITON ® X-100 | | CHAPS | |
|---|---|---|---|---|---|---|
| Protein | Removal (%) | Protein Recovery (%) | Removal (%) | Protein Recovery (%) | Removal (%) | Protein Recovery (%) |
| Insulin (5.7 kD) | 96 | 84 | 98 | 89 | 99 | 84 |
| α-Lactalbumin (14.2 kD) | 96 | 92 | 97 | 86 | 99 | 84 |
| Carbonic Anhydrase (29 kD) | 96 | 92 | 100 | 89 | 99 | 88 |
| Hela Cell Lysate | 98 | 85 | ND | ND | ND | ND |

Examples of suitable column equilibration buffers include, but are not limited, to 0.1M glycine, pH 2.8; 0.15 M NaCl, 0.05% sodium azide, pH 6.75; 0.1 M sodium phosphate, 0.15M NaCl, pH 7.2; 0.05 M ammonium bicarbonate, pH 8.0; and 0.2 M sodium carbonate-bicarbonate buffer, pH 9.4. In one embodiment, the resin is stored in 0.15M NaCl, 0.05% sodium azide, pH 6.75.

In one embodiment, the method is performed at room temperature (i.e., about 20° C. to about 25° C.). In one embodiment, the method is performed at about 4° C.

In one embodiment, protein samples for MS analysis were cell lysates. In one embodiment, protein samples for MS analysis were trypsin digests. In one embodiment, BSA (1 mg/ml) in 50 mM ammonium bicarbonate buffer, pH 8.0, was digested with trypsin overnight at 37° C. (enzyme-to-protein ratio 1:50) in the presence of 1% of each detergent except SDS, which was added after trypsin digestion. In one embodiment, detergent(s) were added after the digestion. Hela cell lysate (1 mg/ml) in 50 mM ammonium bicarbonate buffer, pH 8.0, was digested with trypsin overnight at 37° C. (enzyme-to-protein ratio 1:50) and SDS was added following digestion to a final concentration of 1%. Each digested sample (0.1 ml) containing the detergent was processed through 0.5 ml of Thermo Fisher Detergent Removal Resin® as described above. Control samples (unprocessed) were not processed through the resin. Samples were diluted 1:15 and loaded (1.5 pmol) directly onto a $C_{18}$ column and subjected to LC-MS/MS analysis using a Thermo Scientific LTQ Mass Spectrometer. No trapping column was used. All data were analyzed using MASCOT (Matrix Science). The treated samples had excellent sequence coverage and high MASCOT scores compared to the unprocessed samples. These results indicated successful detergent removal (e.g., FIG. 3).

Detergent elution from the cyclodextrin polymer resin was performed to verify detergent binding. In one embodiment, detergent bound to the resin was eluted with an organic solvent, e.g., 95% ethanol. For example, one ml of HEBC polymer was packed in a column and equilibrated with 0.15 M NaCl, 0.05% sodium azide (buffer). BSA (2 mg/ml) containing 0.1% TRITON® X-100 (2 ml) was applied to the column. The column was then washed with 9 ml buffer to elute the protein free from the detergent. The bound detergent was then eluted with 95% ethanol (4 ml). The column was then washed with water (10 ml) followed by buffer (10 ml). Detergent may be eluted from the resin to permit the resin to be reused after thorough washing to ensure solvent removal. The regenerated resin can be reused.

In one embodiment, BSA trypsin digests were prepared and treated by the inventive method using a spin column. Post-column samples were analyzed by LC-MS/MS, followed by data analysis using MASCOT (Matrix Science Inc., London UK) and Scaffold (Proteome Software Inc., Portland Oreg.) software. The post-column samples had excellent sequence coverage and high MASCOT scores, indicating successful removal of detergents from the samples. Sequence coverage indicates how much sequence or identity of the target protein was identified. The MASCOT score indicates how well each spectrum is matched with the theoretical spectrum, which is based on probability.

Figure 2A:
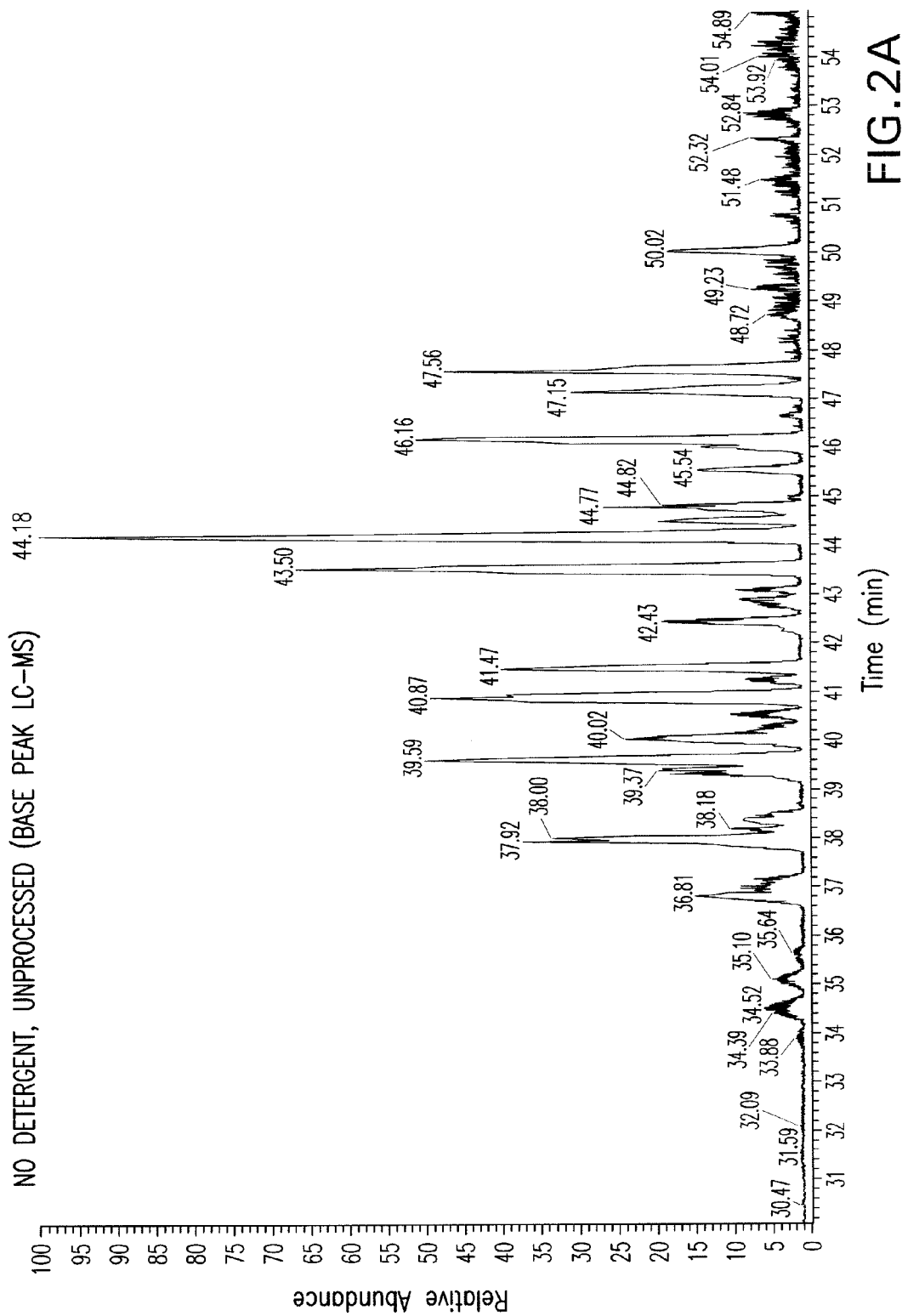
FIG. 2A-2P shows mass spectrometry (MS) analysis of bovine serum albumin (BSA) tryptic peptides with and without detergent.
Figure 2B:
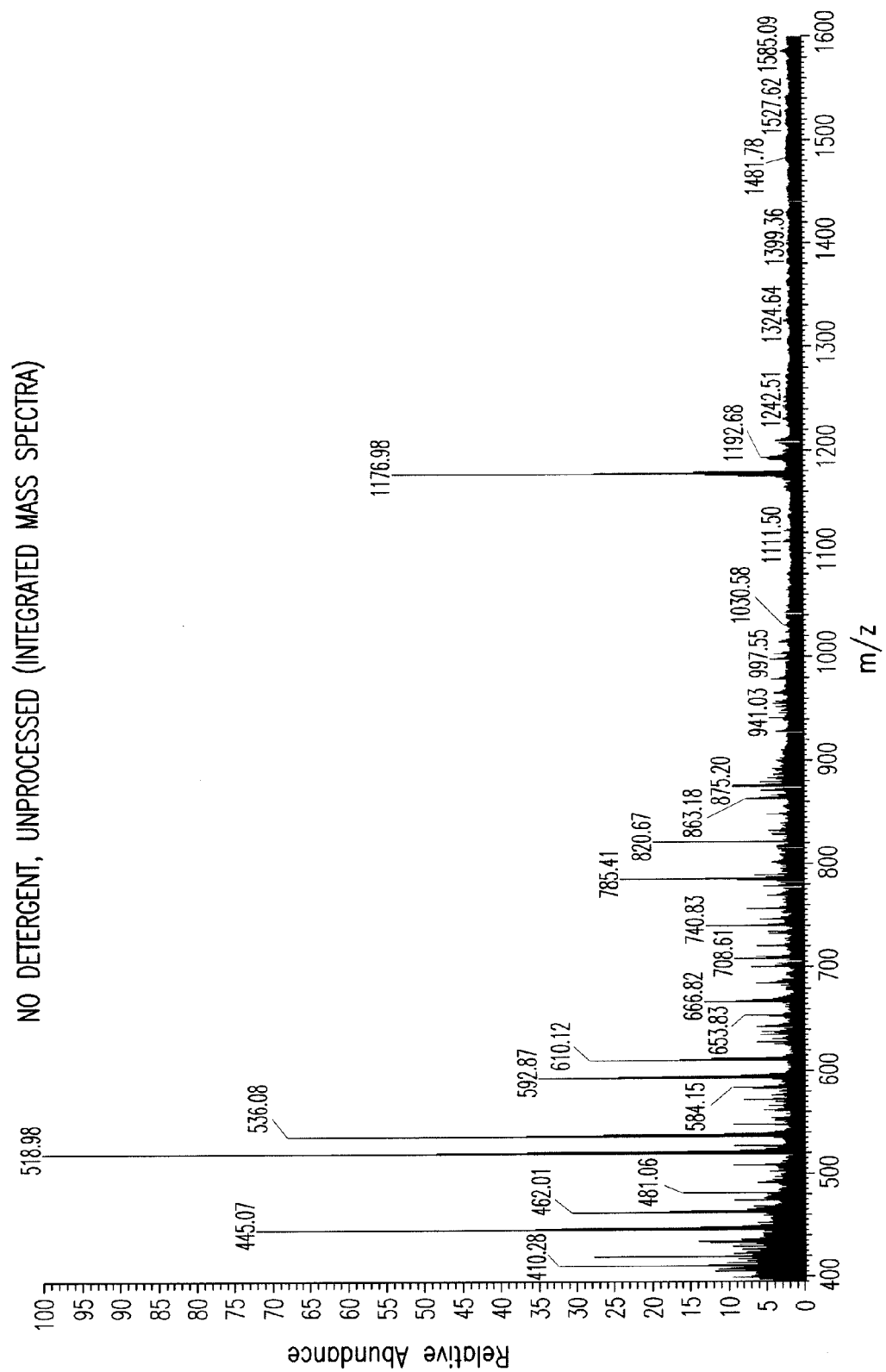
Figure 2C:
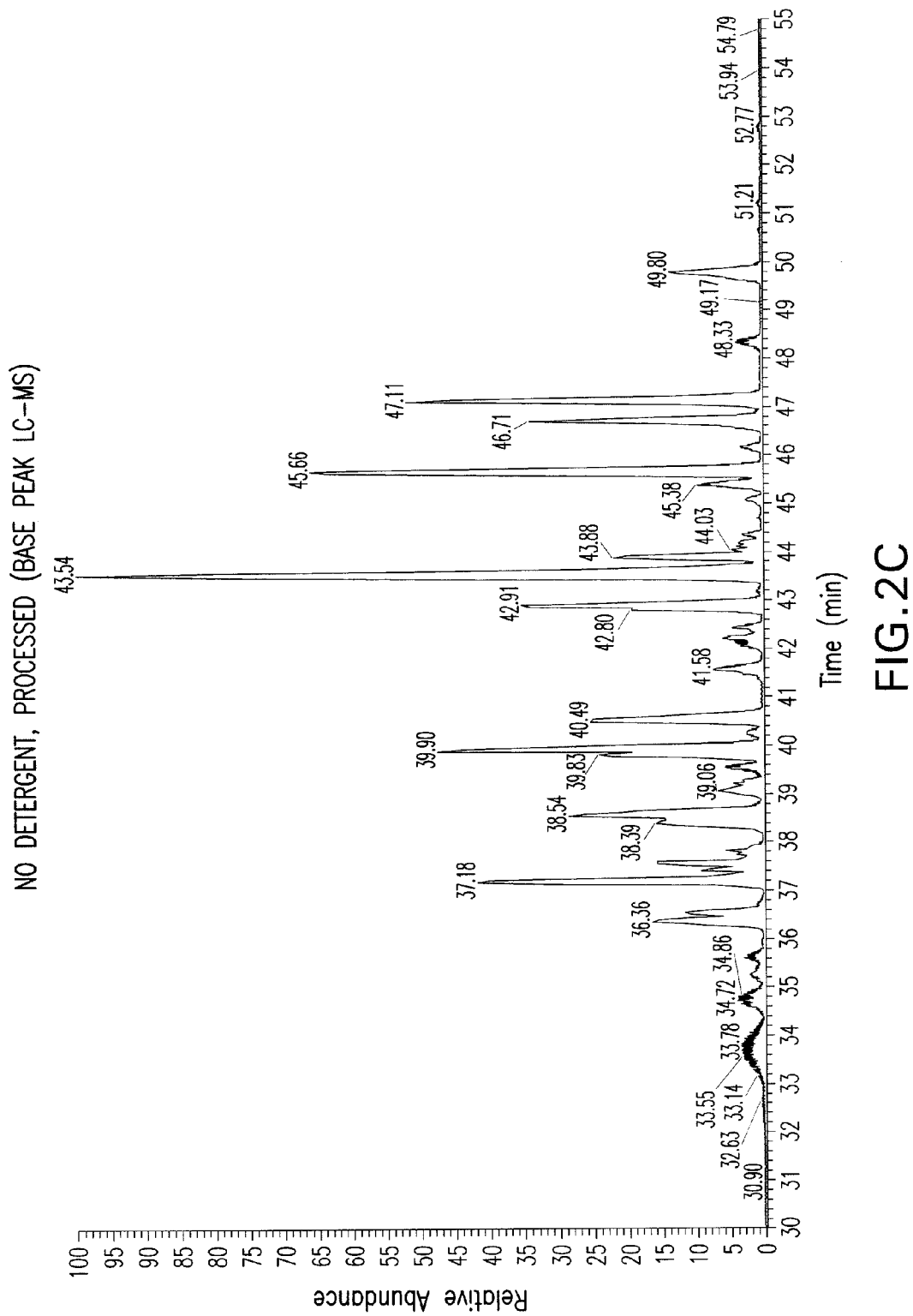
Figure 2D:
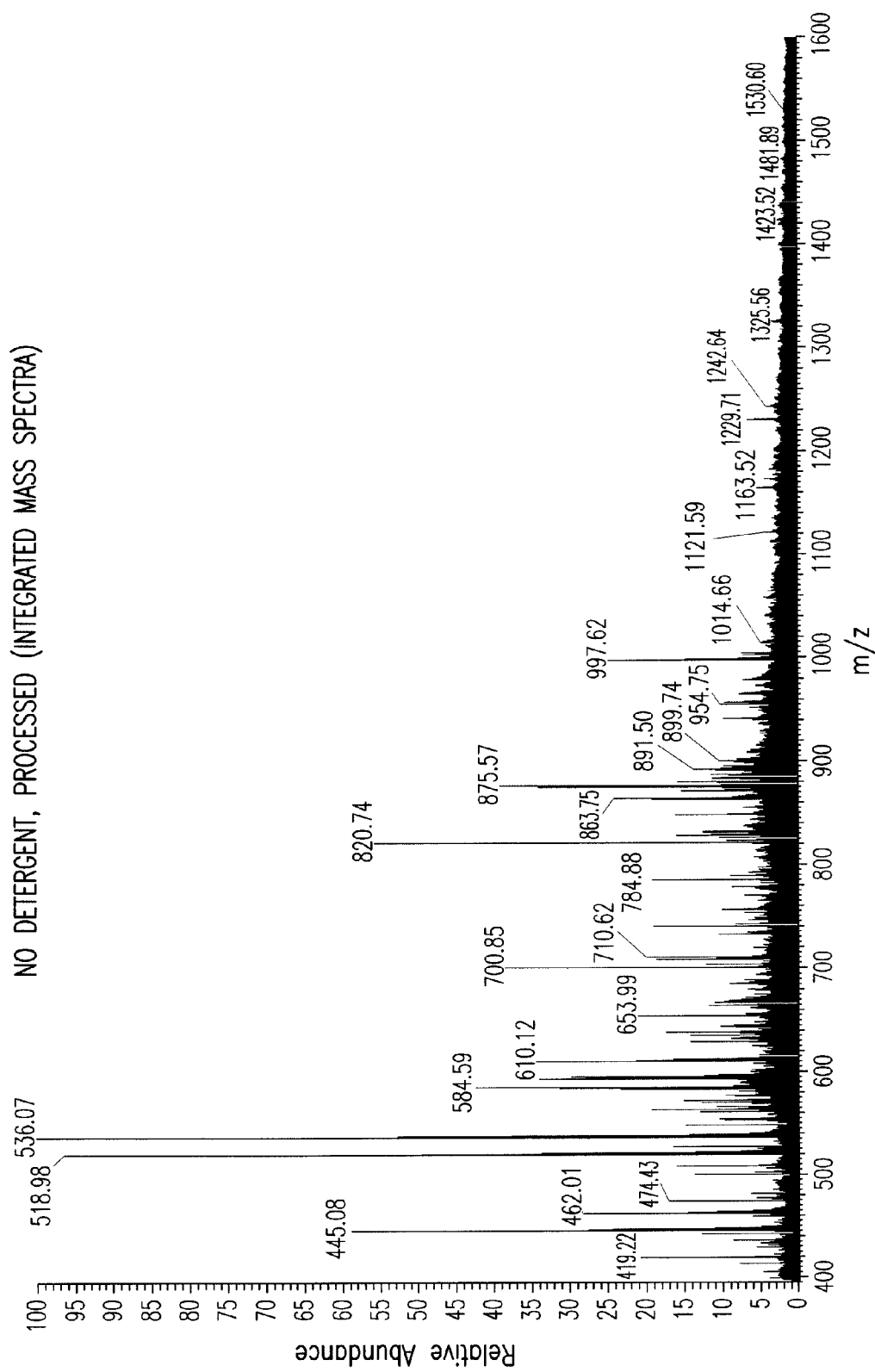
Figure 2E:
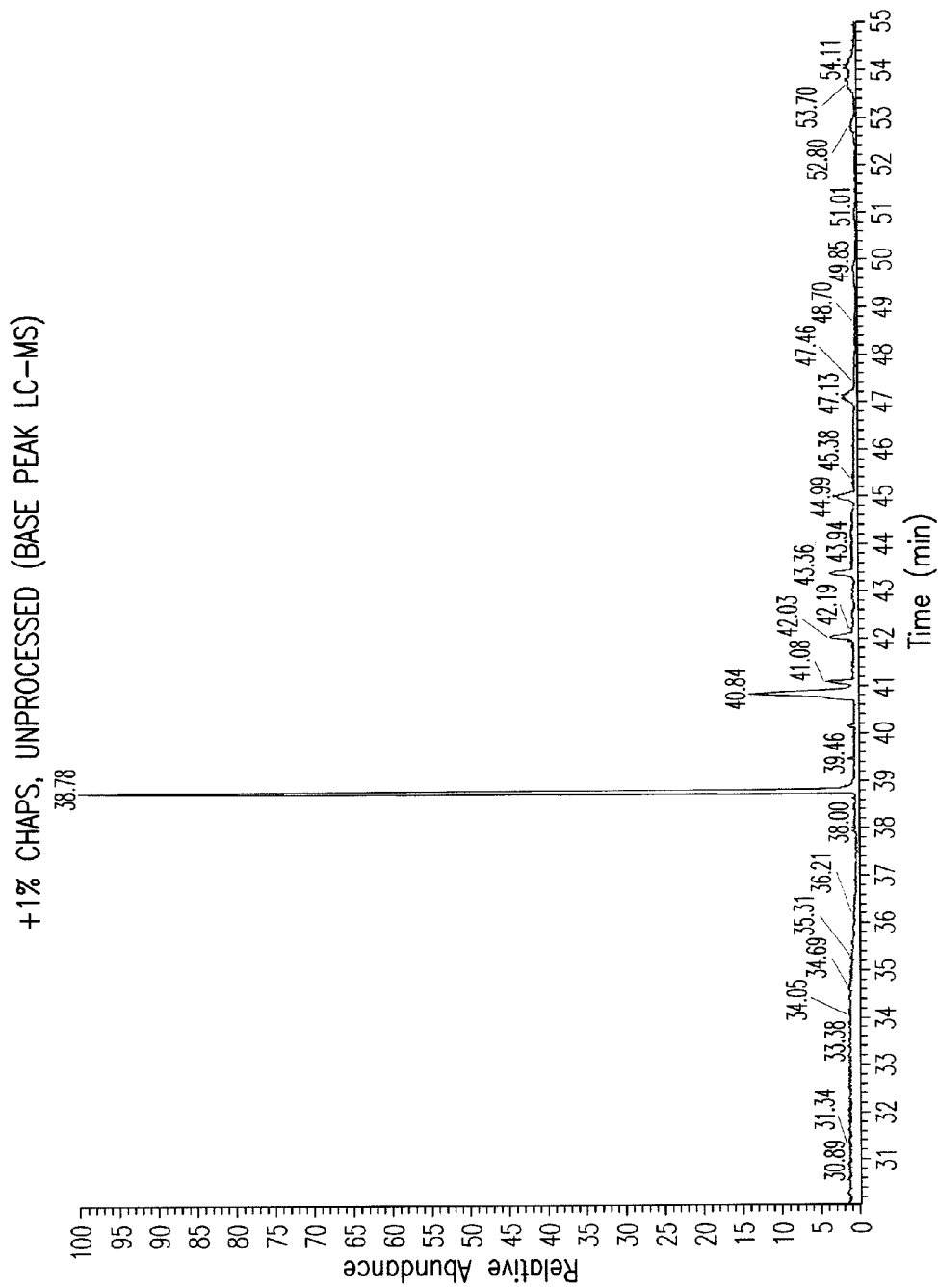
Figure 2F:
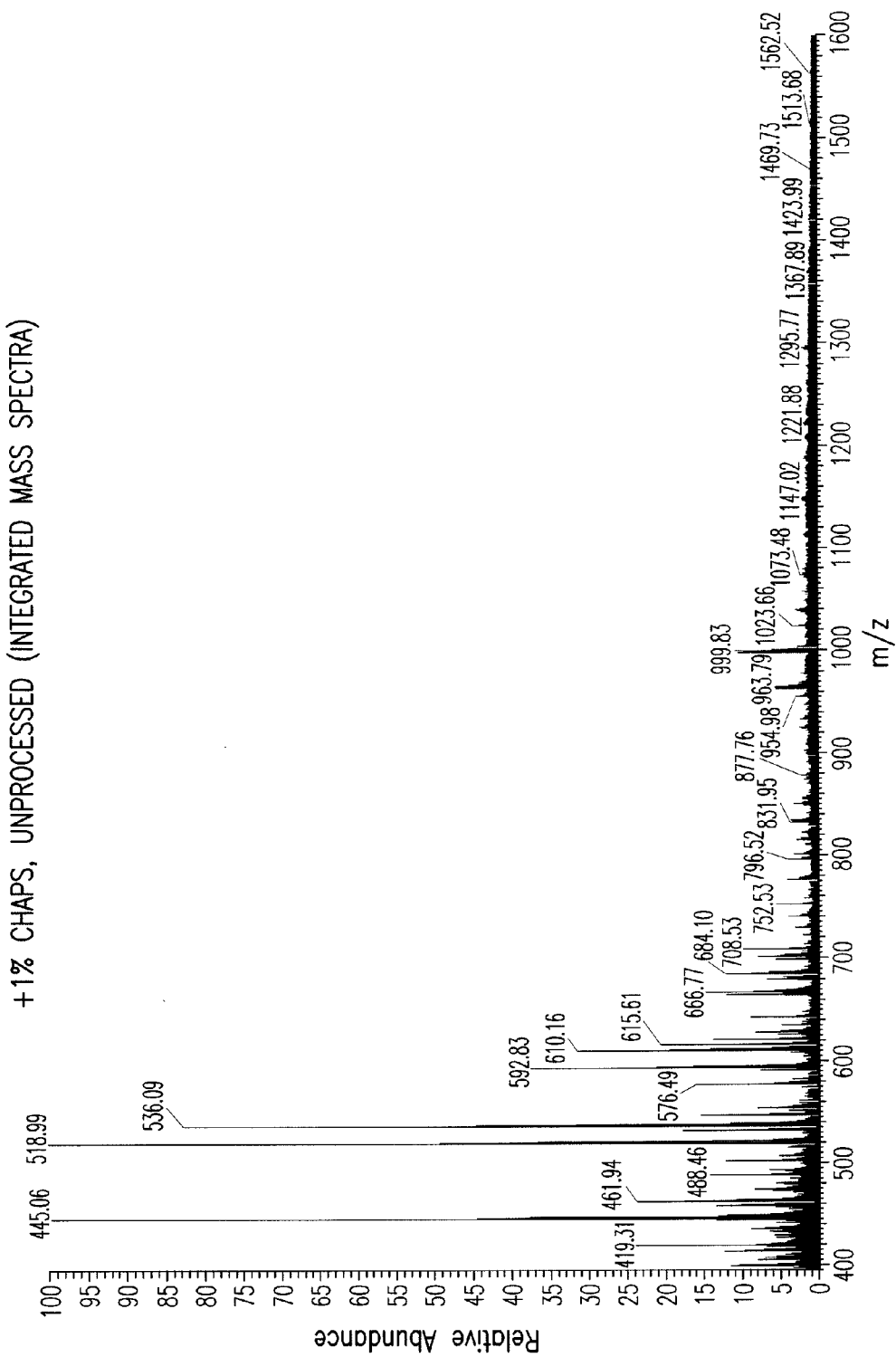
Figure 2G:
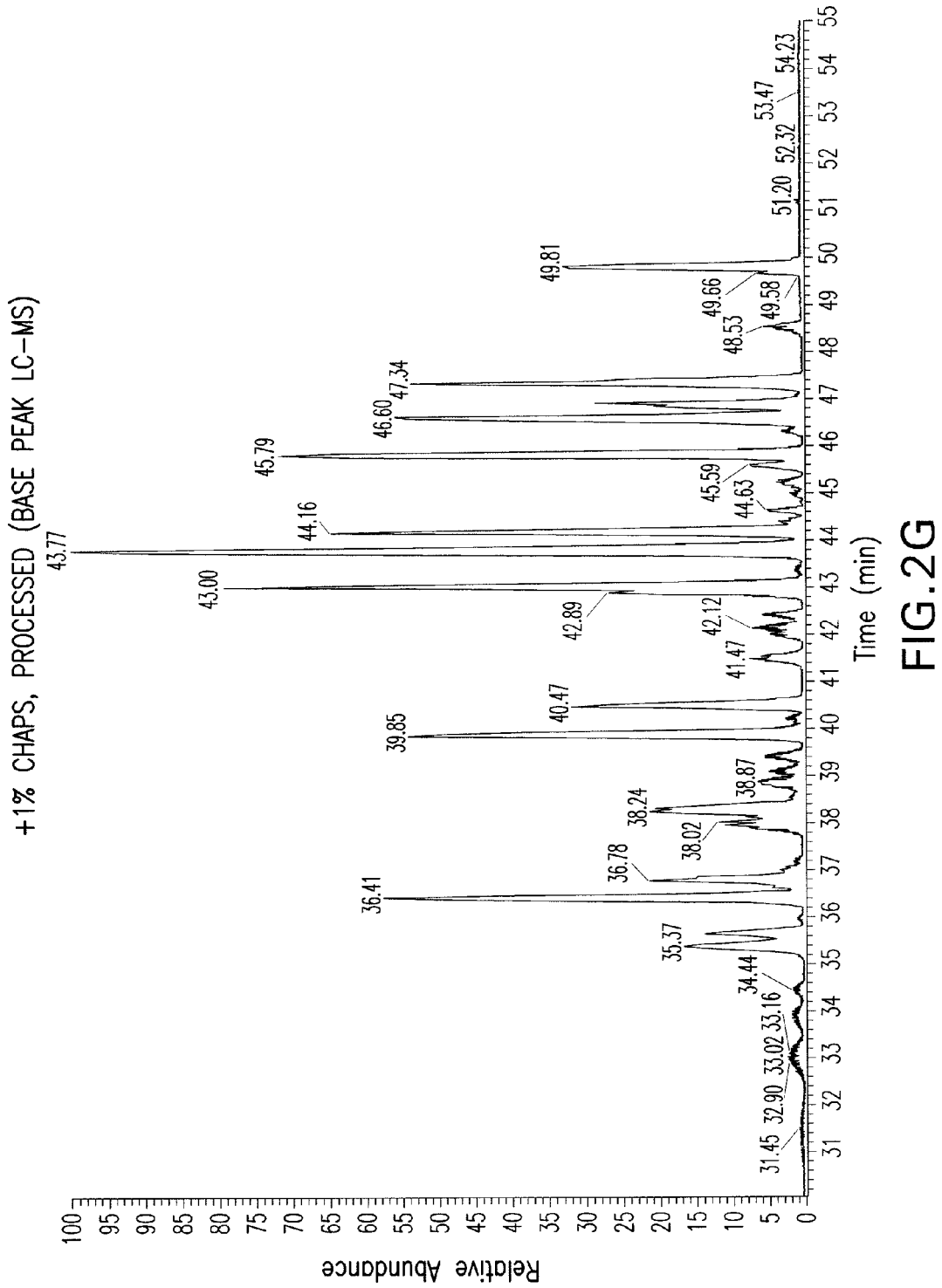
Figure 2H:
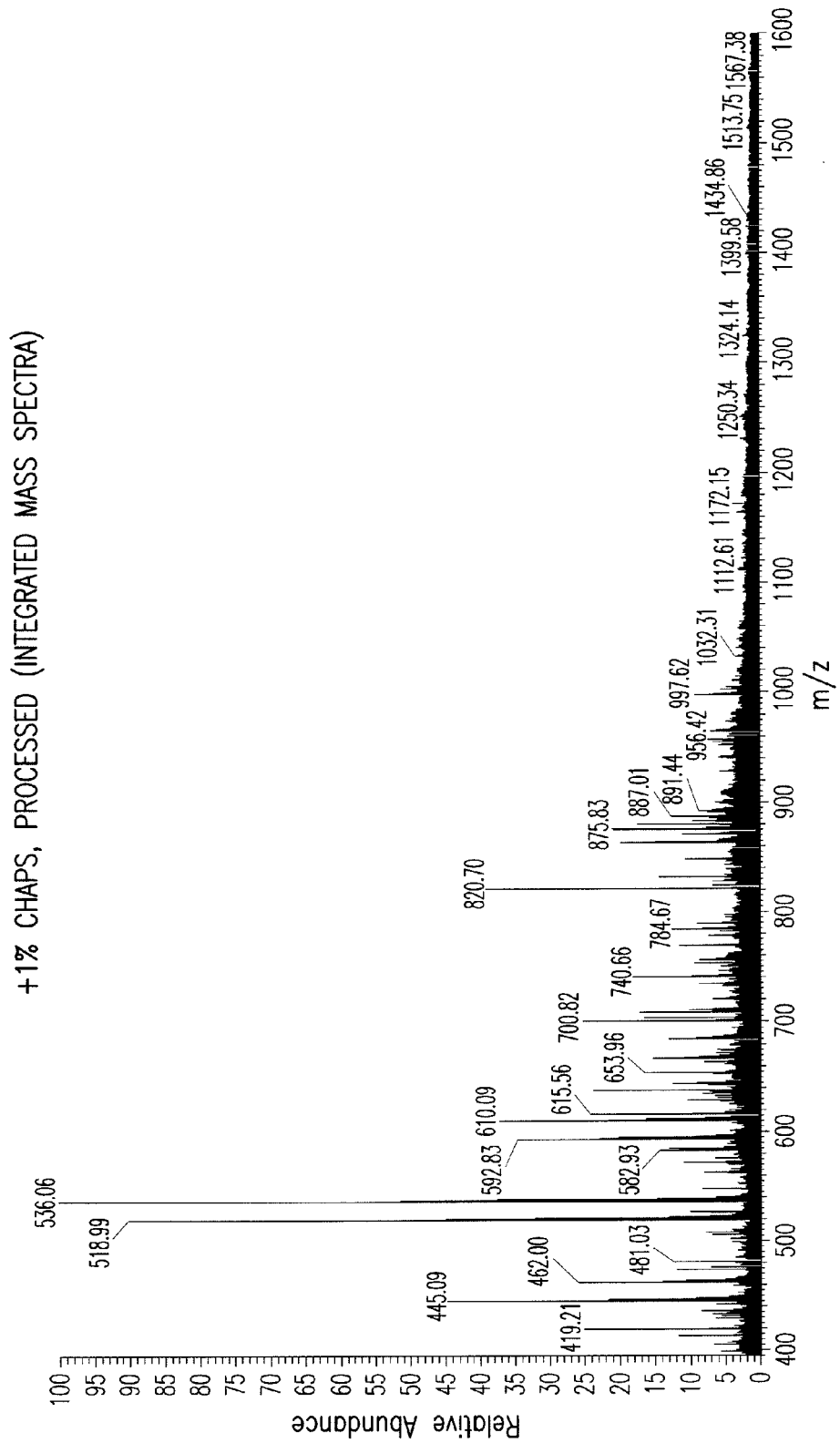
Figure 21:
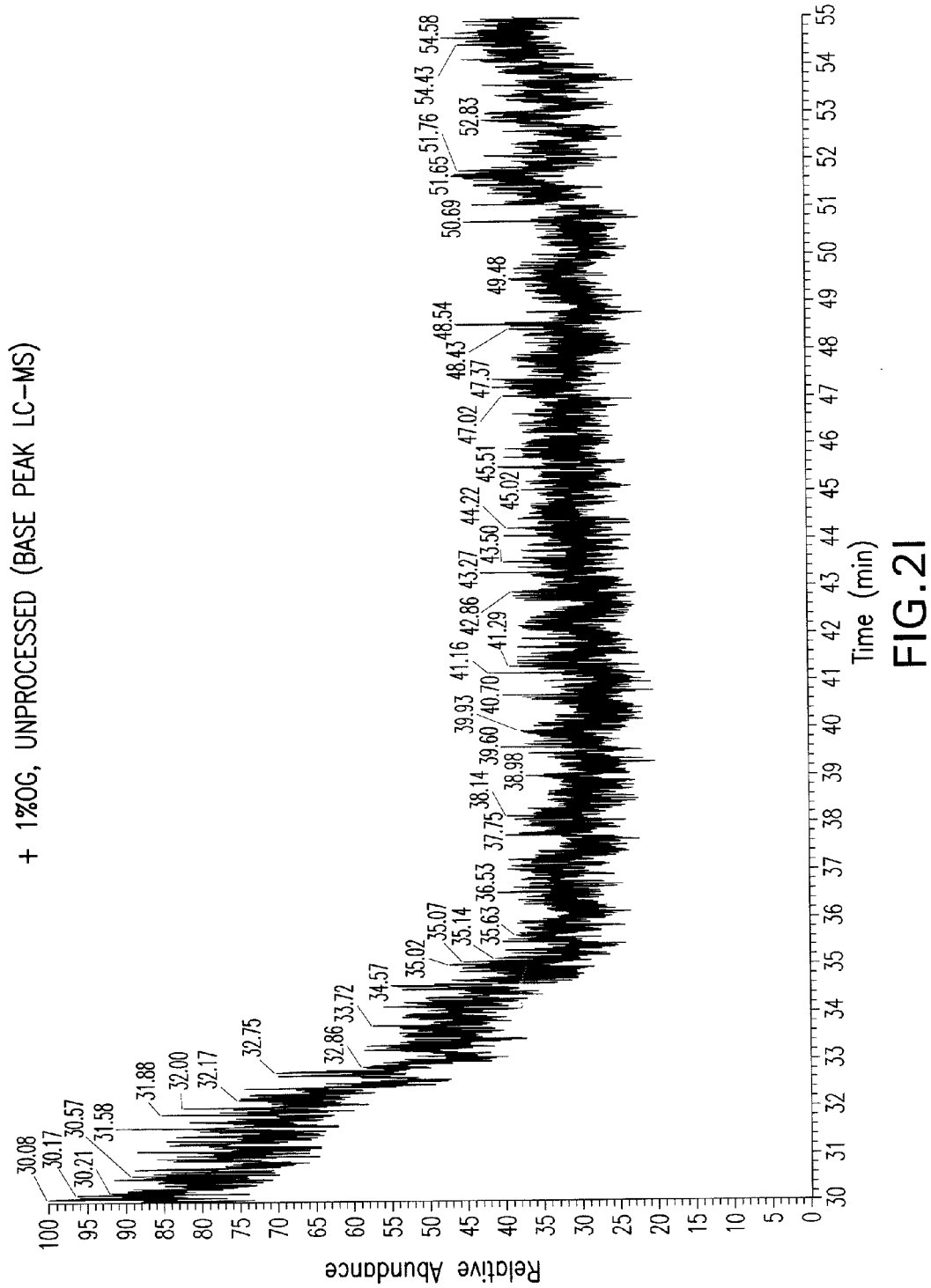
Figure 2J:
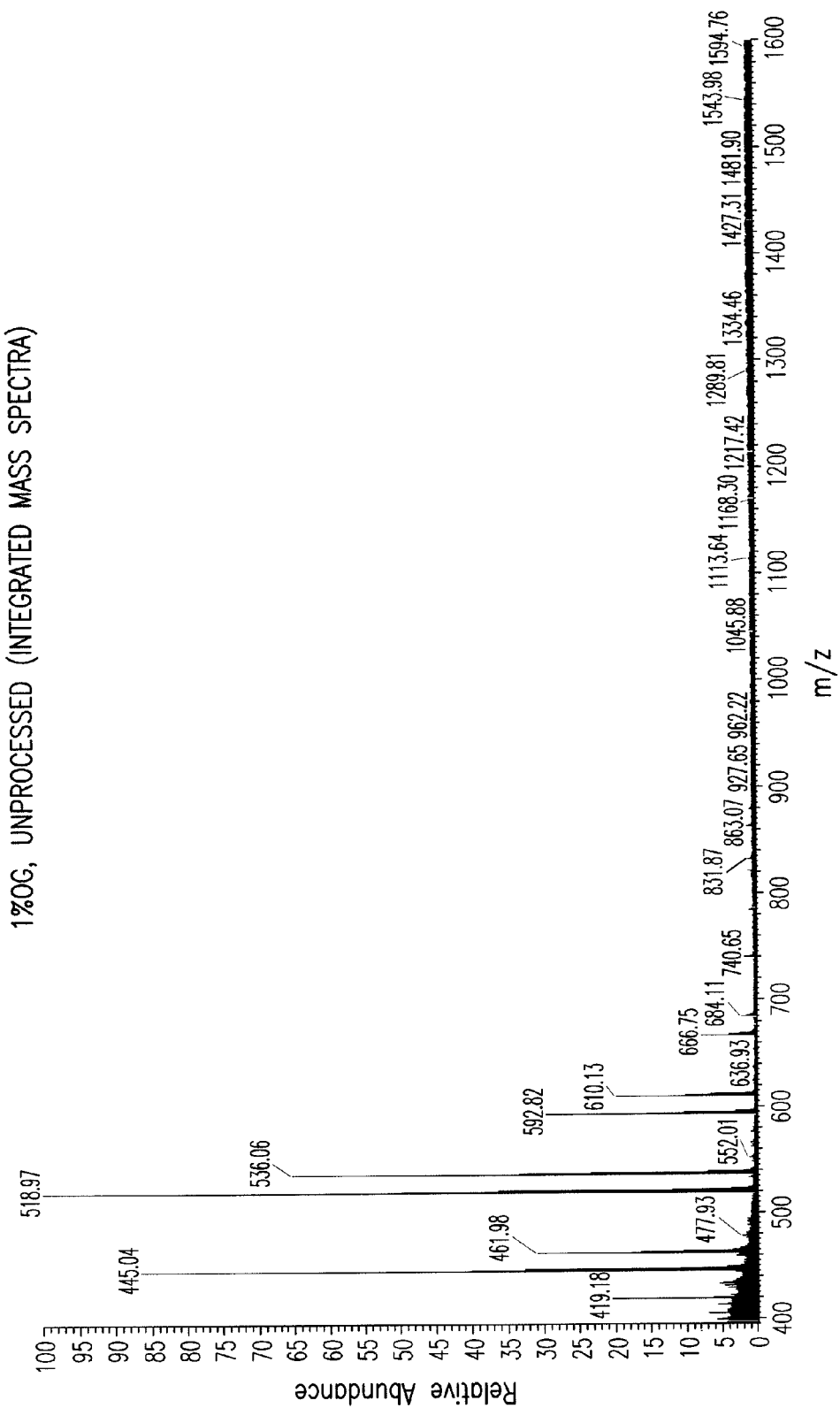
Figure 2L:
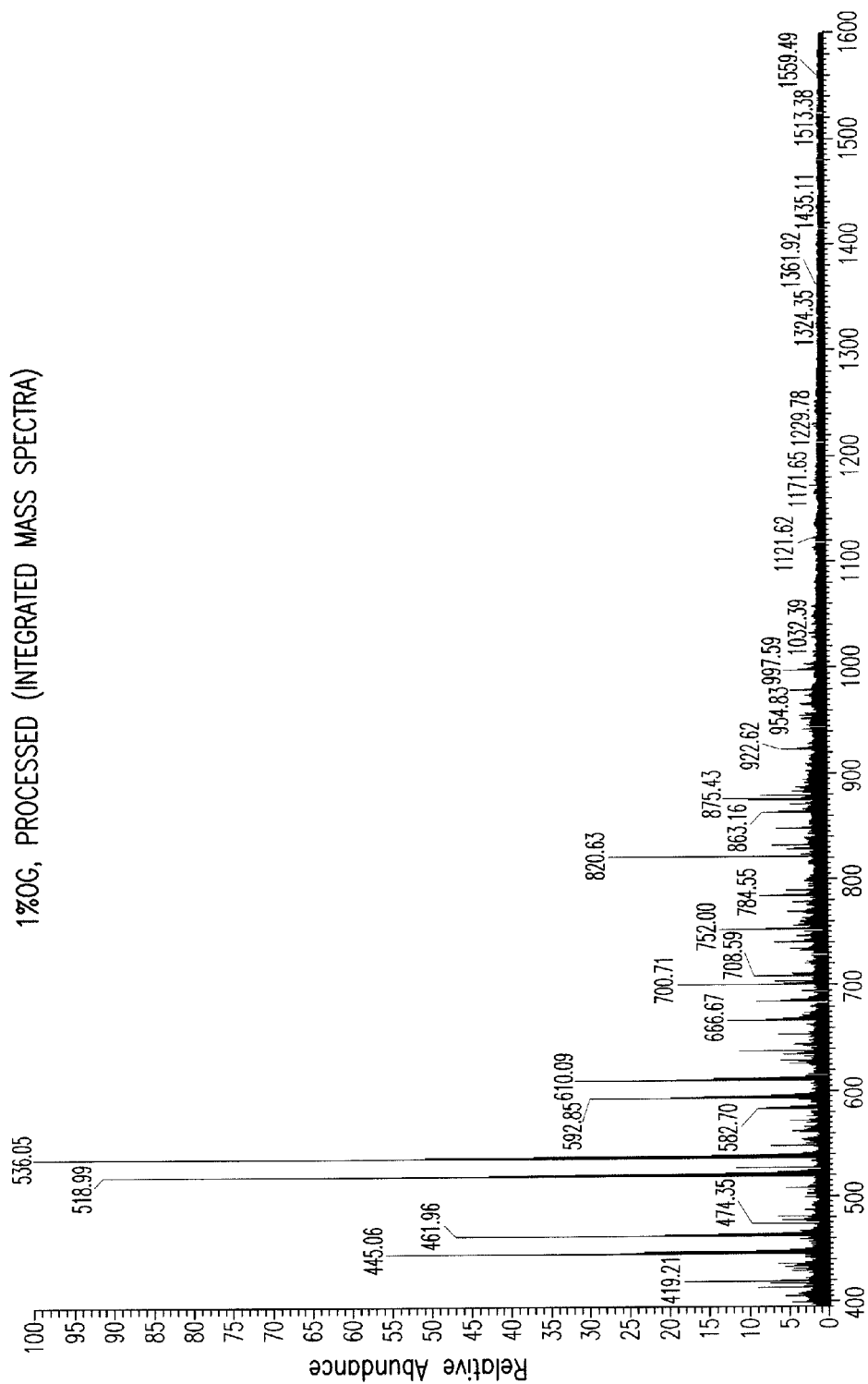
Figure 2M:
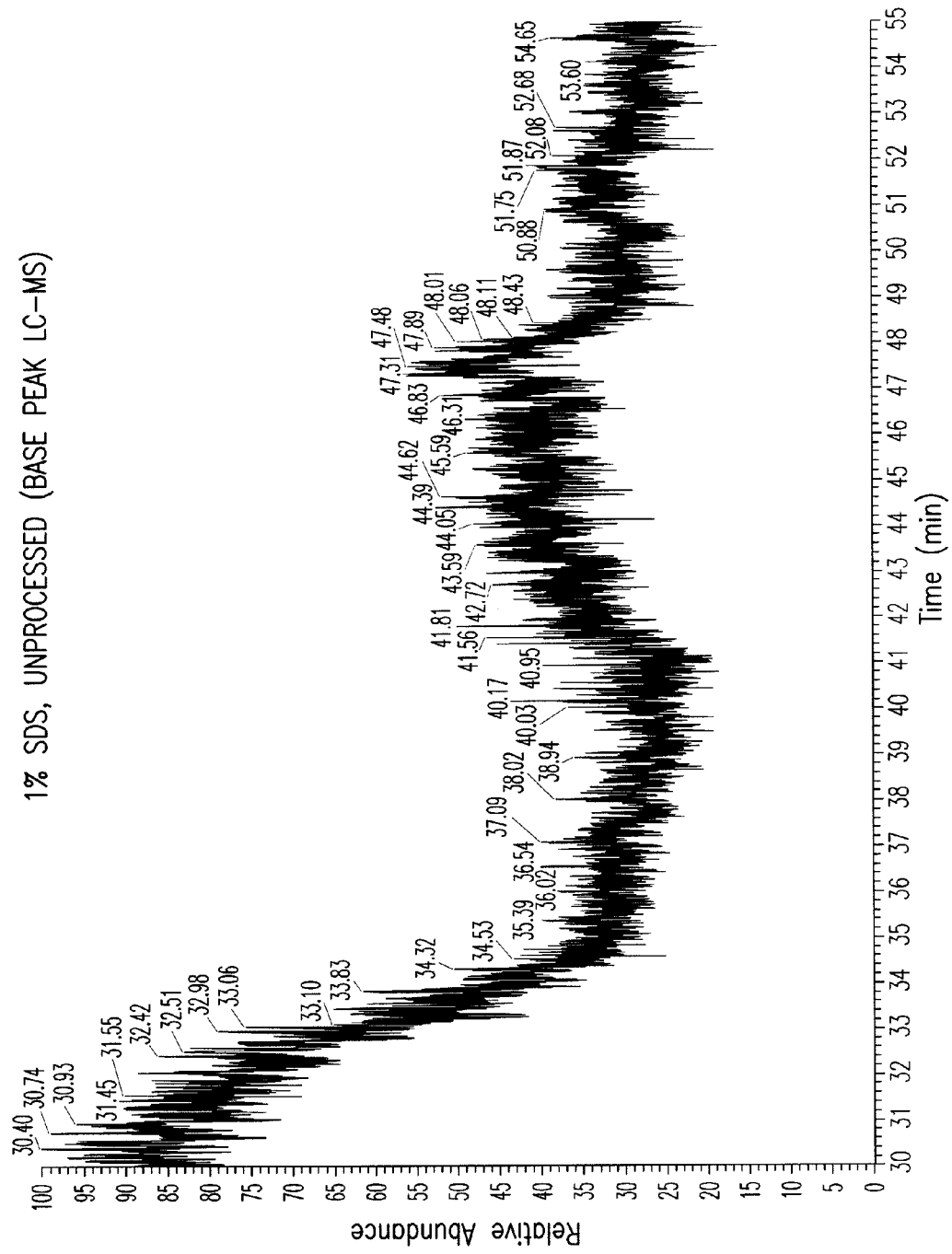
Figure 2N:
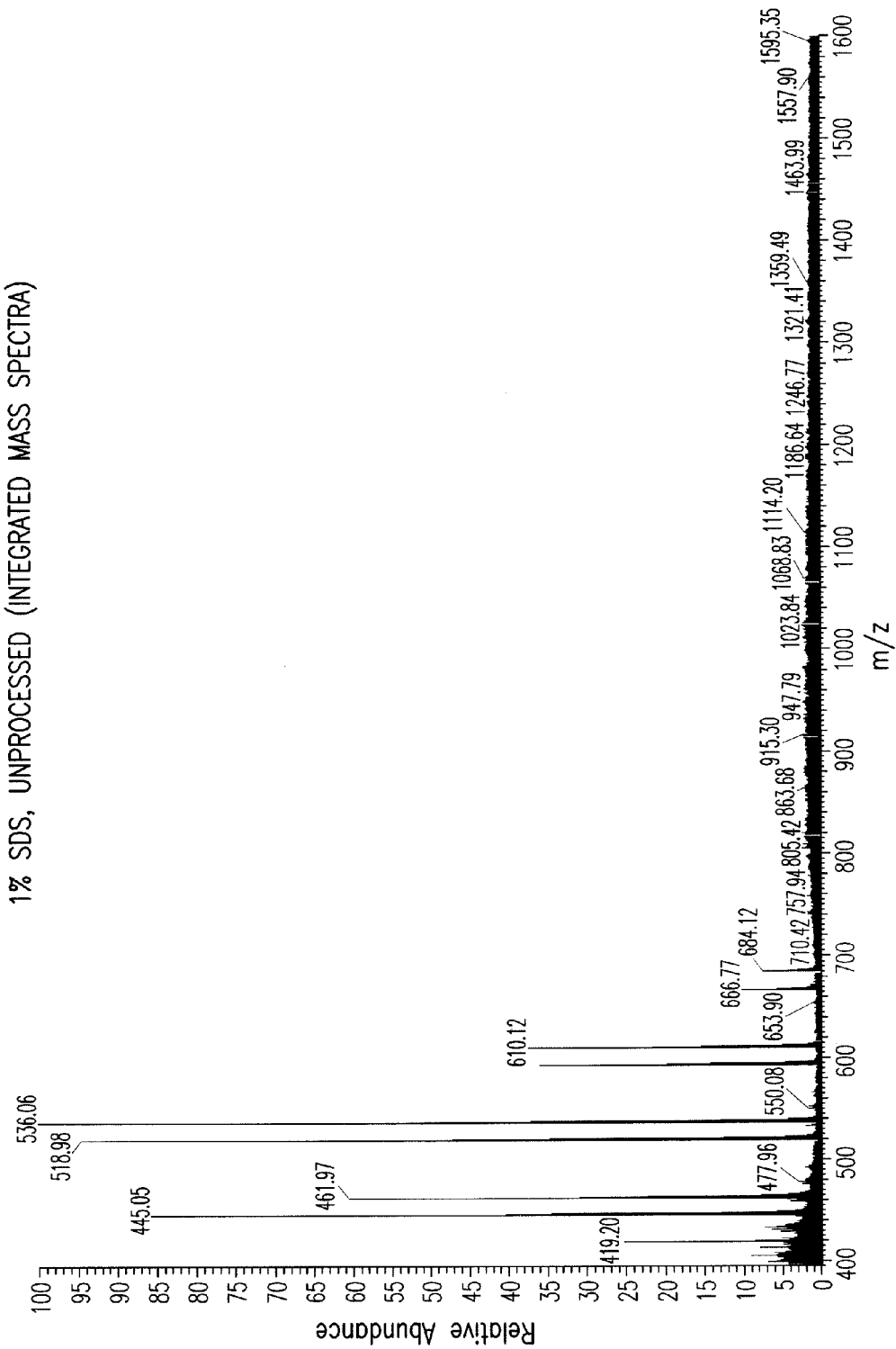
Figure 20:
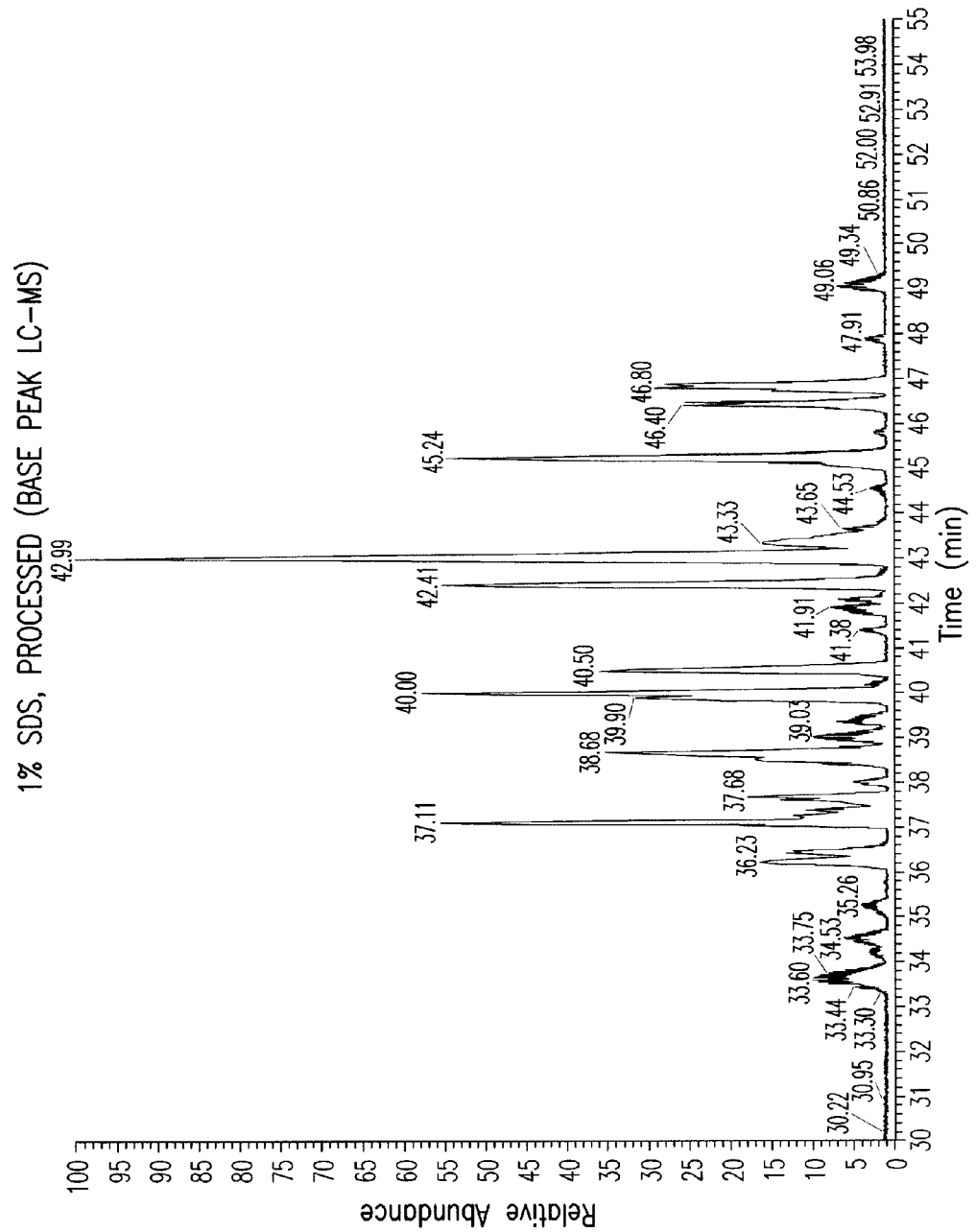
Figure 2P:
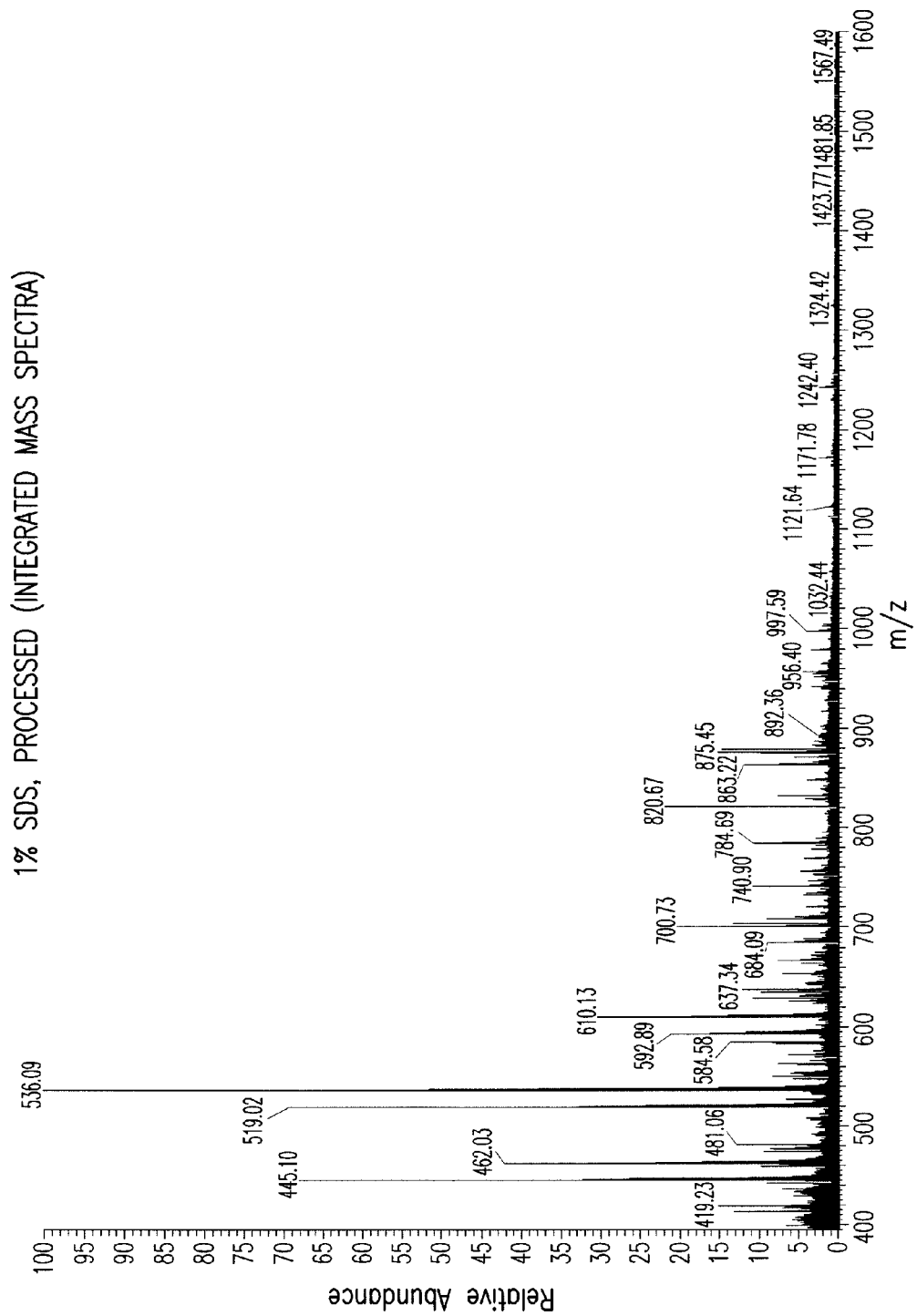

FIG. 2A-2P shows spectrogram results from samples, containing exemplary detergents at exemplary concentrations, that had not been treated by the disclosed method (unprocessed) and treated by the disclosed method (processed). The base peak LC-MS chromatograms and the integrated mass spectra are shown. X-axis was time in minutes, and Y-axis was relative abundance. These results demonstrated that the resin effectively removed detergents from protein digests without loss of peptides, and eliminated detergent interference, as shown by reduction in the noisy baseline when processed samples are compared with unprocessed samples. Samples containing BRIJ-35, lauryl maltoside, octyl thioglucoside, TRITON® X-100, TRITON® X-114, NP-40, and sodium deoxycholate subjected to the resin also showed successful detergent removal from the protein digest without loss of peptides, and eliminated detergent interference (data not shown).

Figure 3:
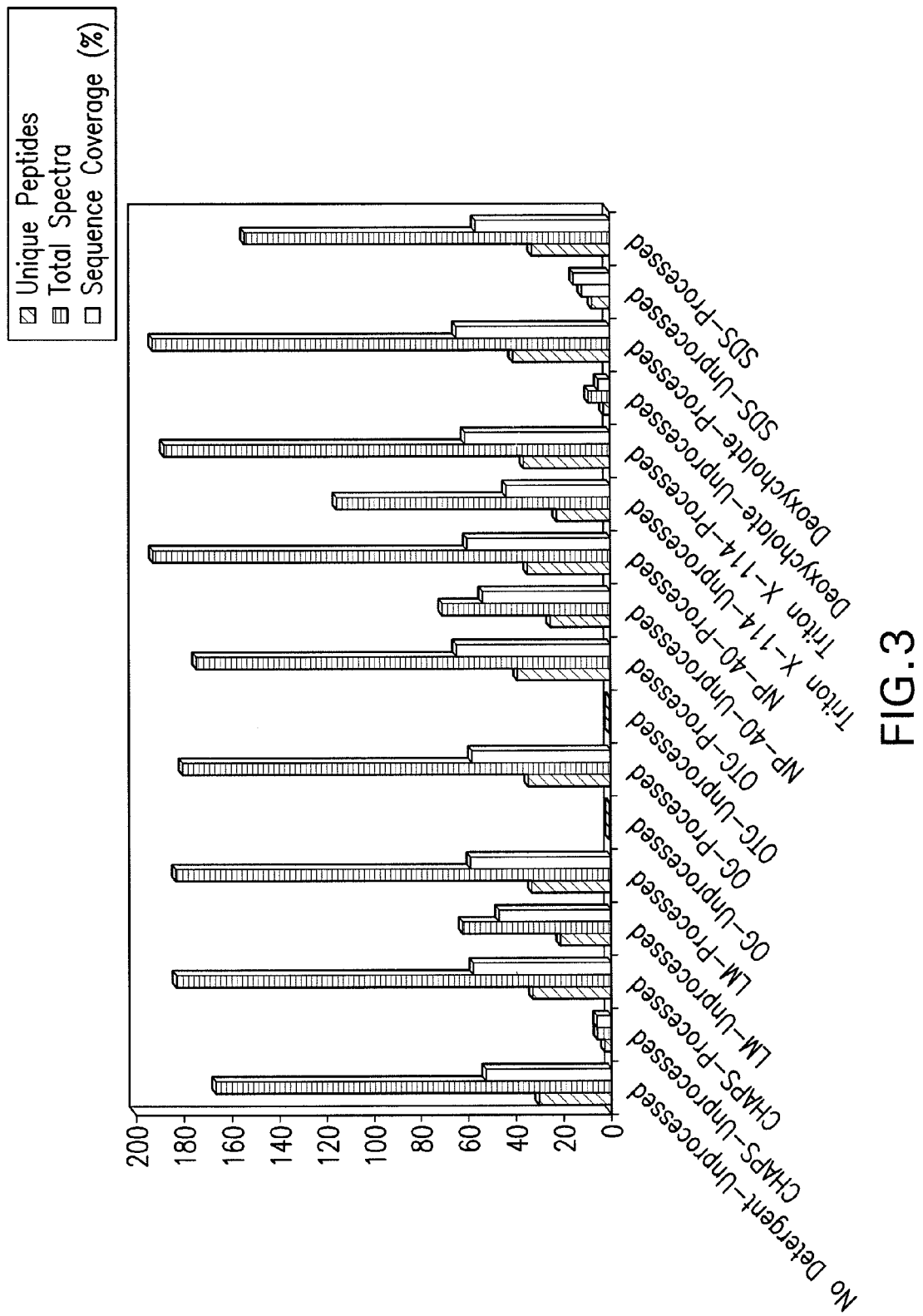
FIG. 3 compares MS/MS analysis of BSA tryptic peptides in processed and unprocessed samples.
Figure 4A:
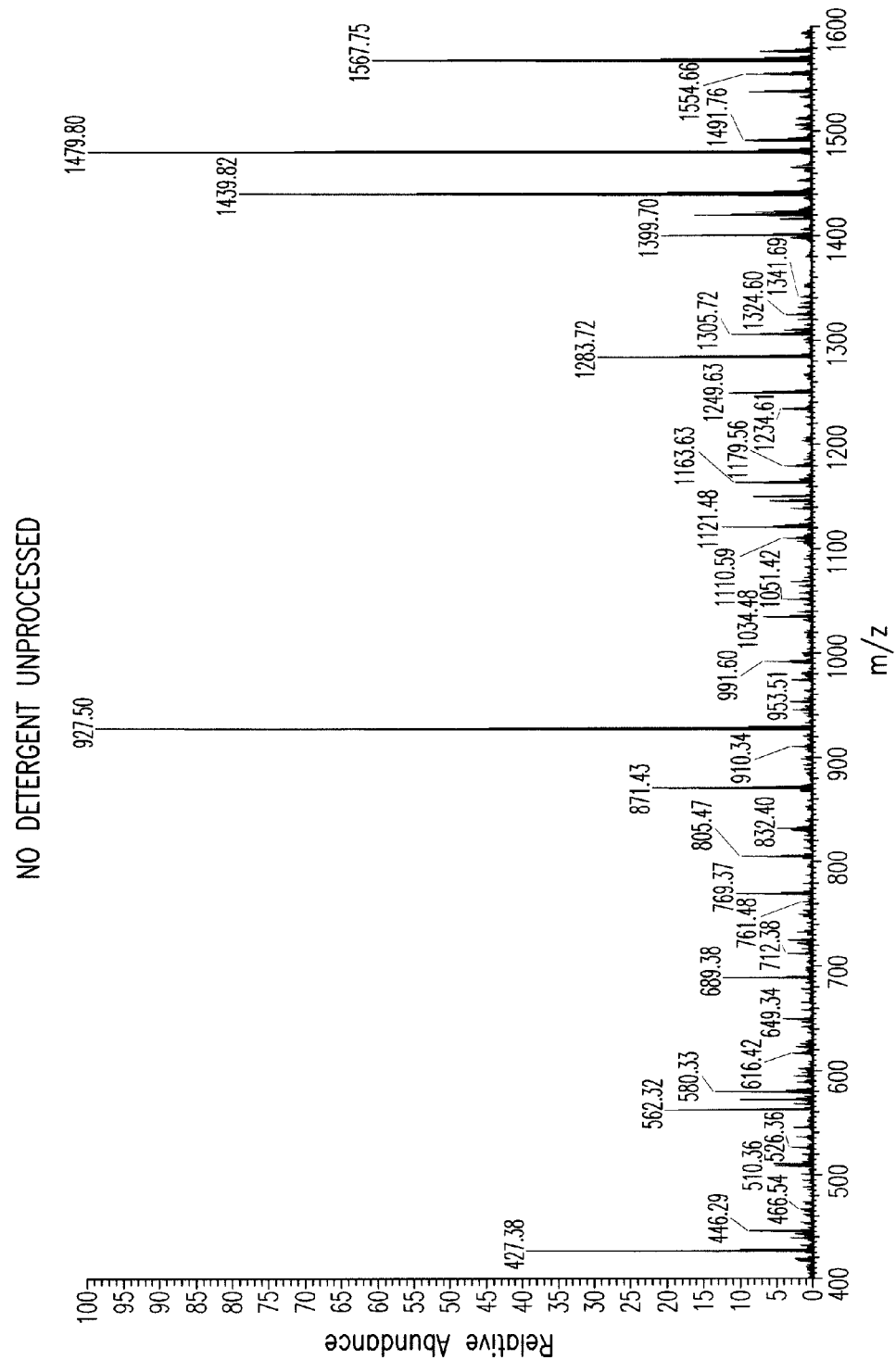
FIG. 4A-4H shows Matrix-Assisted Laser Desorption Ionization (MALDI)-MS analysis of BSA tryptic peptides with and without detergent The resin is polymerized cyclic glucose oligosaccharides, i.e., polymerized cyclodextrins. For example, α-, β-, and γ-cyclodextrins contain, respectively, 6, 7, and 8 sugar molecules. Cyclodextrin rings are both hydrophilic and hydrophobic, i.e., amphipathic. They can be topologically represented as bottomless bowl structures. The bowl interior is considerably less hydrophilic than the aqueous exterior environment, and thus able to host hydrophobic molecules. The bowl exterior is sufficiently hydrophilic to impart water solubility. The sugar hydroxyl groups may be derivatized to modify the cyclodextrin physical and/or chemical properties.
Figure 4B:
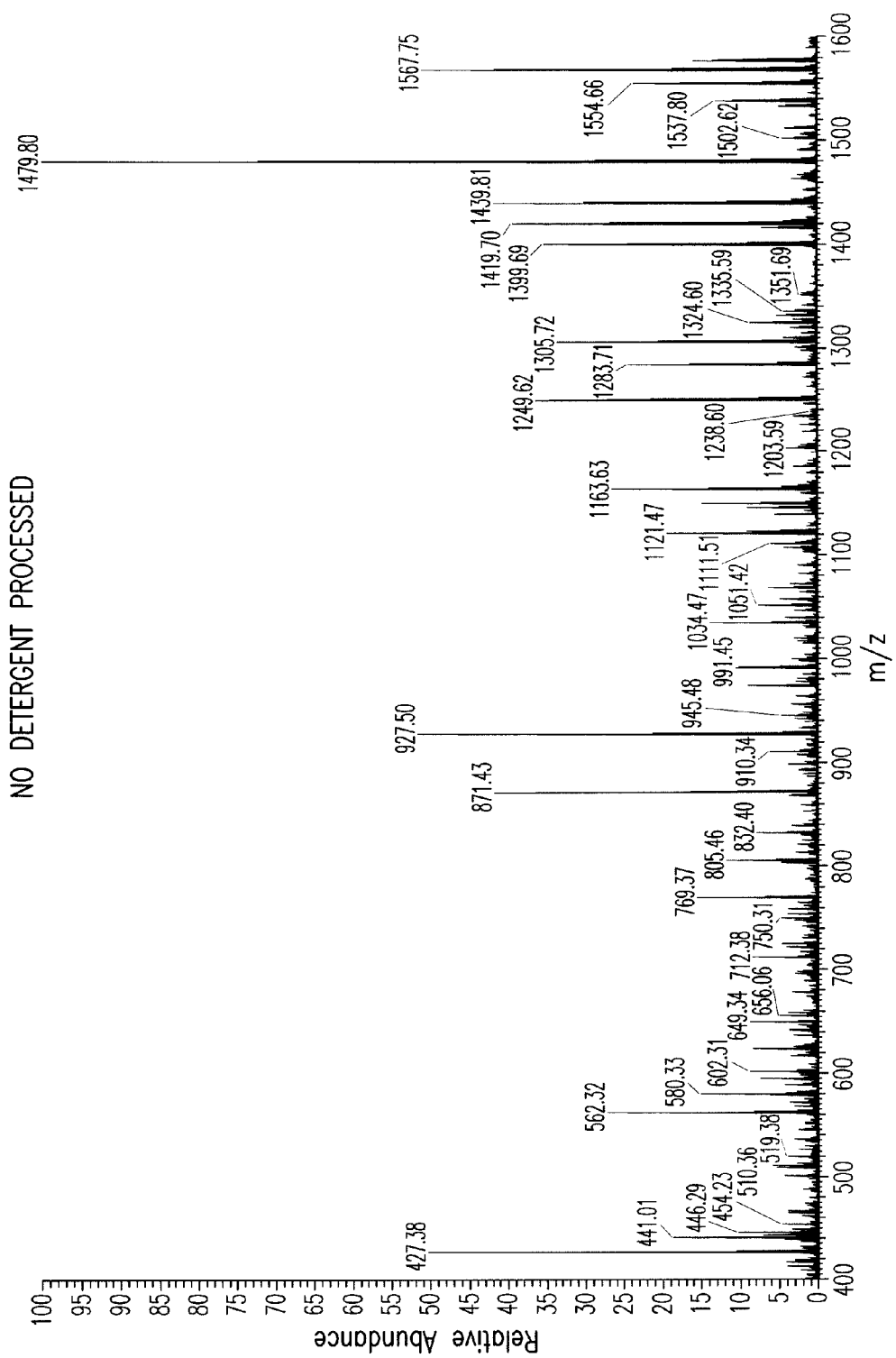
Figure 4C:
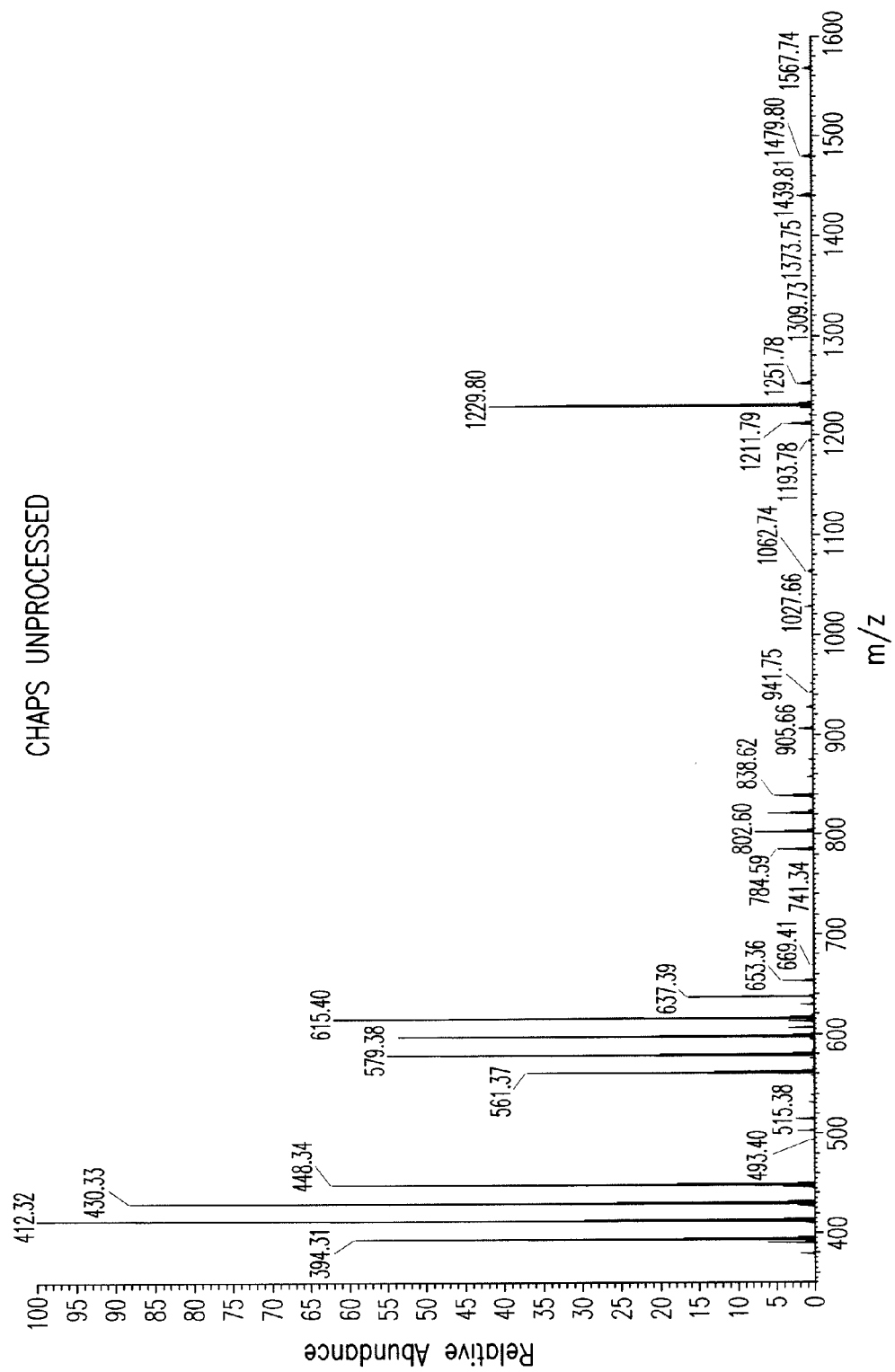
Figure 4D:
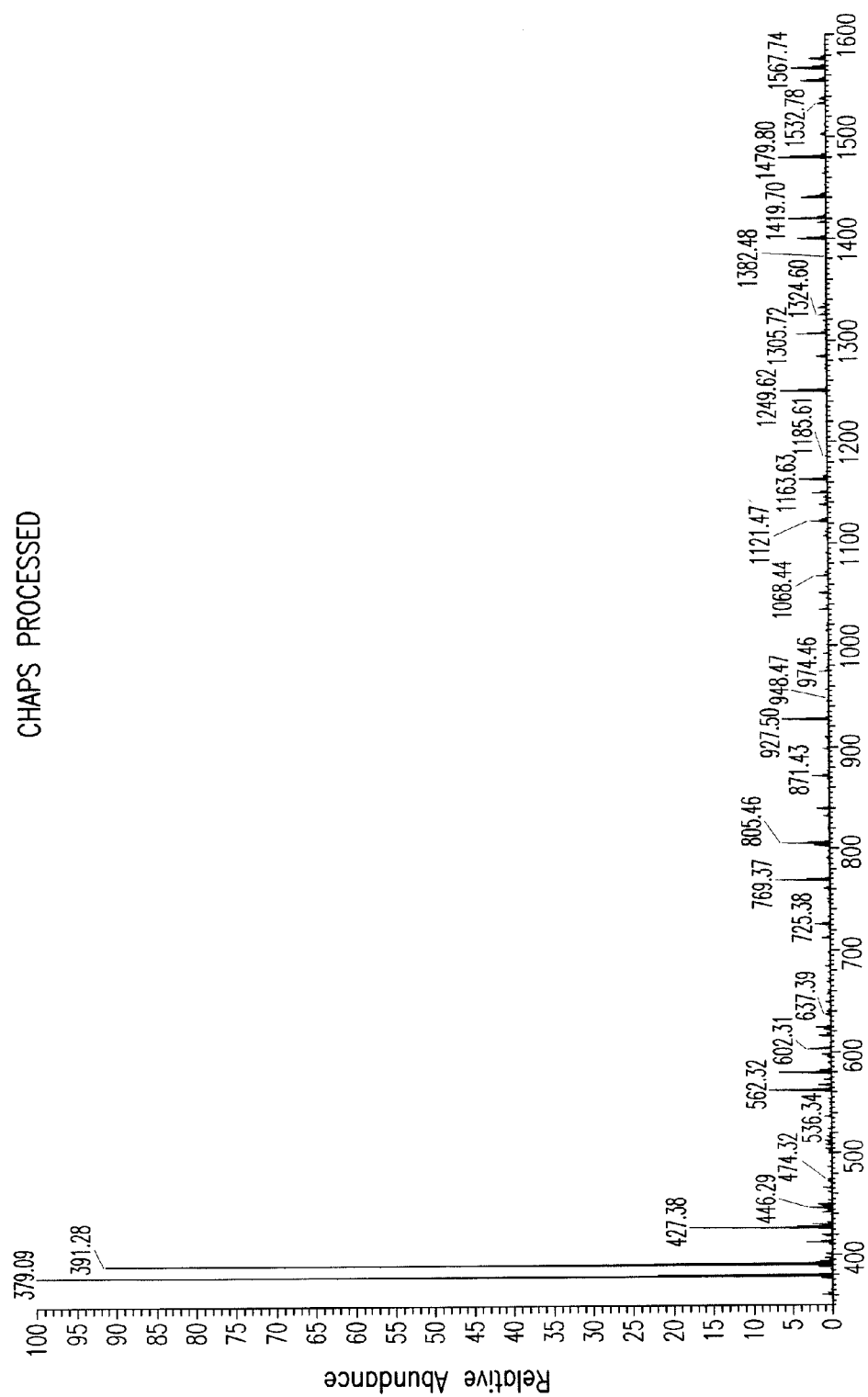
Figure 4E:
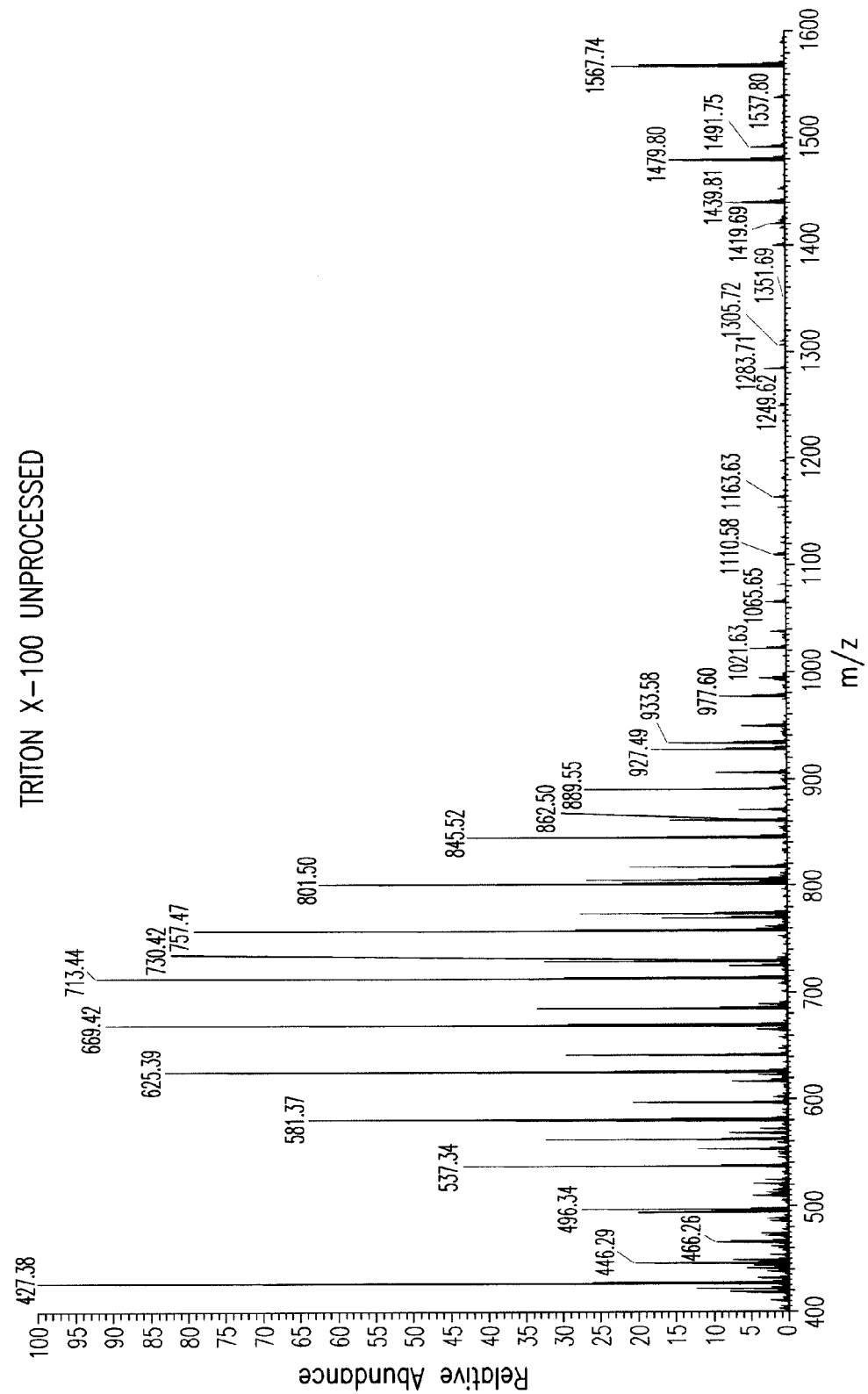
Figure 4F:
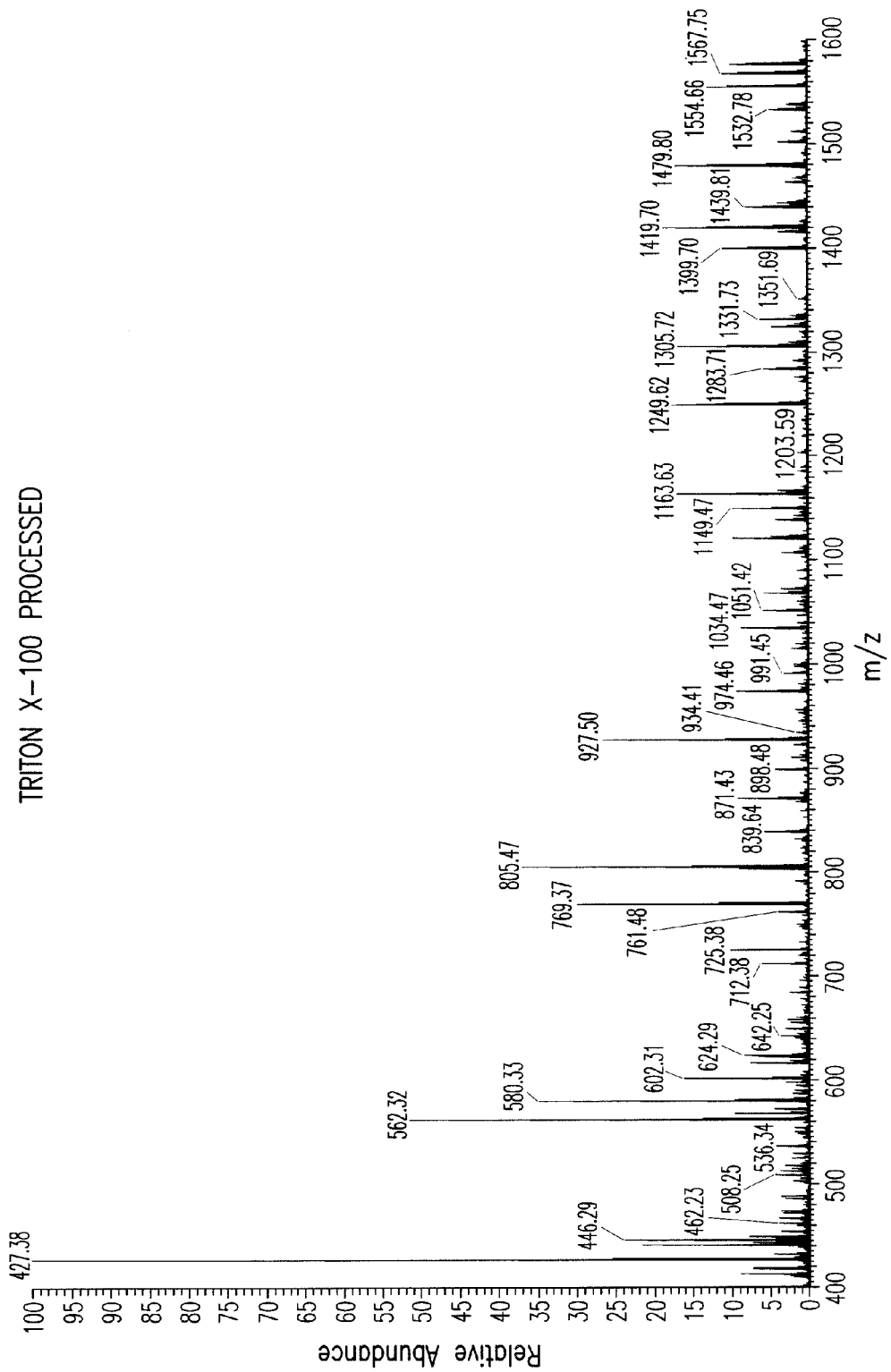
Figure 4G:
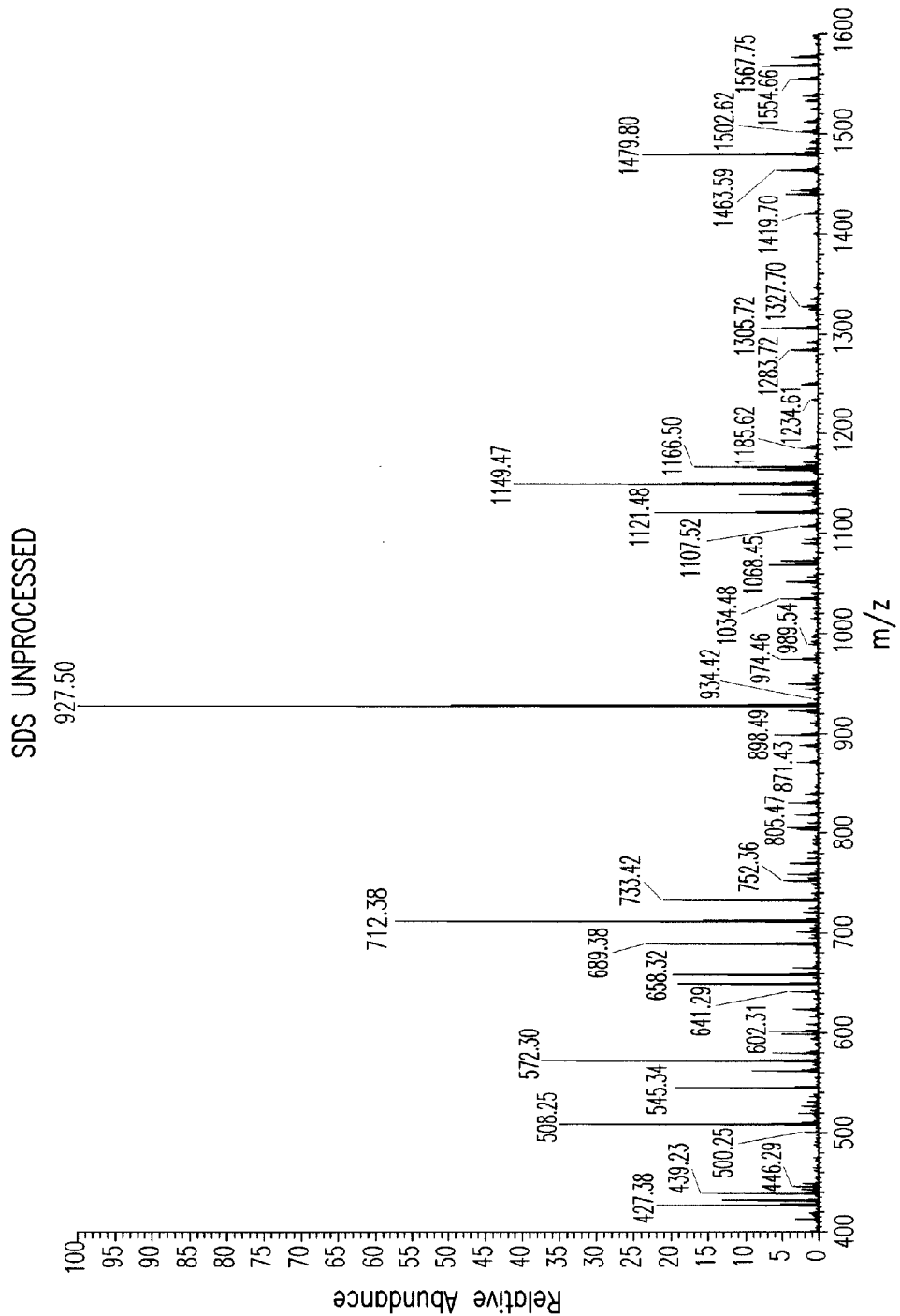
Figure 4H:
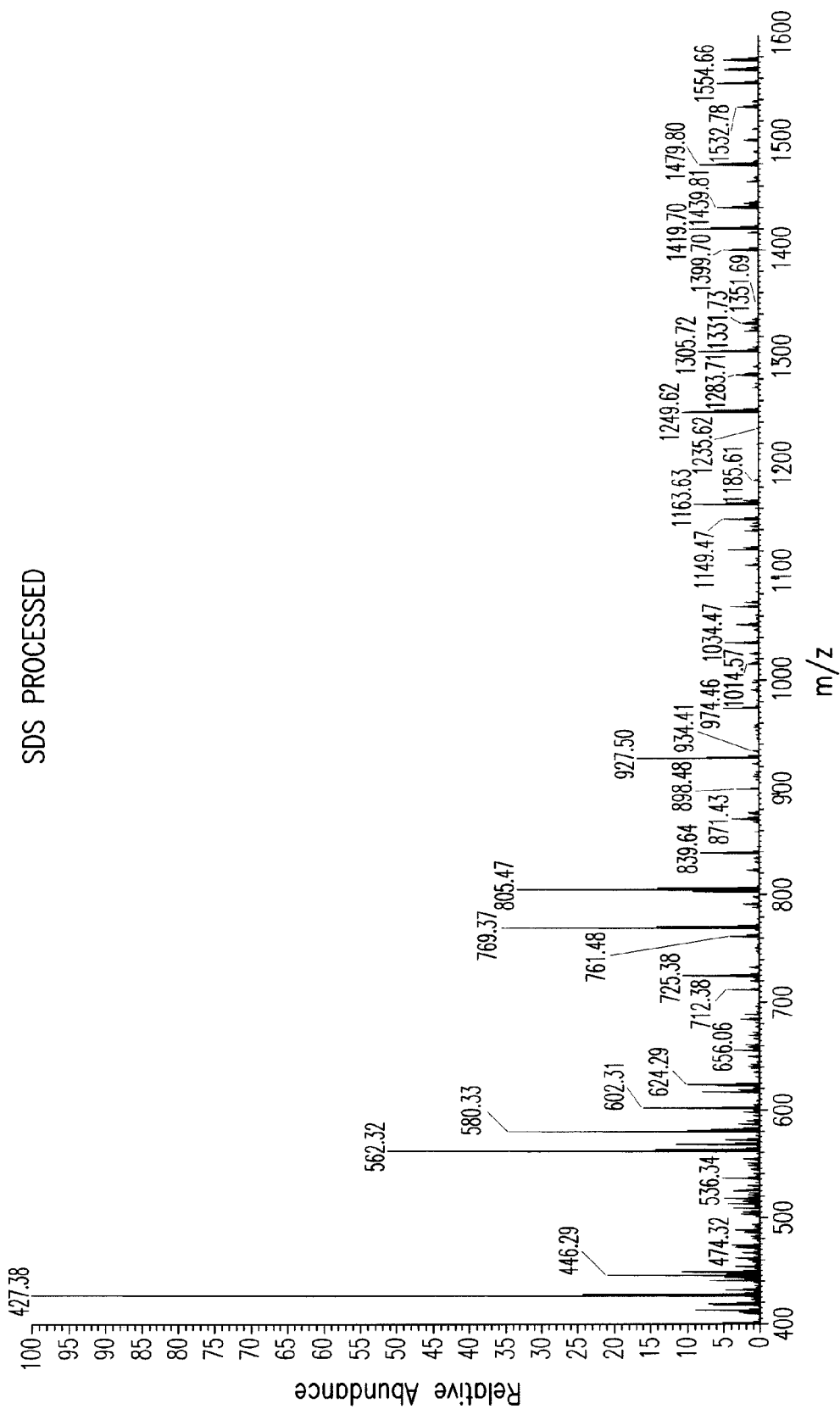

FIG. 3 shows unique peptides, total spectra, and percent sequence coverage data from unprocessed samples containing no detergent, processed samples containing no detergent, and processed samples containing representative detergents. Unique peptides are those that are unique to the target protein. Total spectra are the total number of peptide spectra for a given protein, which correlates to the abundance of the protein. BSA (1 mg/ml) in 50 mM ammonium bicarbonate buffer, pH 8.0, was digested with trypsin overnight at 37° C. (enzyme-to-protein ratio 1:50) in the presence of 1% of each detergent except SDS, which was added after trypsin digestion. Each digested sample (0.1 ml) containing the detergent was processed through 0.5 ml of Thermo Fisher Detergent Removal Resin® as described above. Control samples (unprocessed) were not processed through the resin. Samples were diluted 1:15 and loaded (1.5 pmol) directly onto a C18 column and subjected to LC-MS/MS analysis using a Thermo Scientific LTQ Mass Spectrometer. No trapping column was used. All data were analyzed using MASCOT. Y-axis was arbitrary units. The results showed excellent sequence coverage and high MASCOT scores, indicating successful detergent removal from the protein digest.

FIG. 4A-4H shows results of MALDI analysis of unprocessed and processed samples. BSA (1 mg/ml) in 50 mM ammonium bicarbonate buffer, pH 8.0, was digested with trypsin overnight at 37° C. (enzyme-to-protein ratio 1:50) in the presence of 1% of each detergent except SDS, which was added after trypsin digestion. Each digested sample (0.1 ml) containing the detergent was processed through 0.5 ml of Thermo Fisher Detergent Removal Resin® as described above. Control samples (unprocessed) were not processed through the resin. Samples were diluted 1:15 and loaded (1 pmol) on to a Thermo MALDI-Orbitrap Mass Spectrometer. Alpha-cyano 4-hydroxy cinnamic acid (5 mg/ml) was used in a matrix with acetonitrile/water/0.1% TFA as a co-solvent. Data were processed with XCALIBER® Qual Browser 2.0 (Thermo Fisher Scientific, San Jose Calif.). The results clearly demonstrated successful detergent removal by the resin without the loss of peptides, and eliminated interference by detergents. Samples containing TRITON® X-114, NP-40, and sodium deoxycholate subjected to the resin also showed successful detergent removal without the loss of peptides (data not shown).

The method efficiently removed about ≧95% of detergent from biological protein-containing samples, while maintaining at least about 84% protein and peptide recovery from the samples. In the spin column format, the procedure was simple, efficient, and rapid, taking less than about 15 minutes.

Other variations or embodiments of the invention will also be apparent to one of ordinary skill in the art from the above figures and descriptions. Thus, the forgoing embodiments are not to be construed as limiting the scope of this invention.

What is claimed is:

1. A method to prepare a biological sample for mass spectroscopy analysis, the sample containing at least one protein and at least one detergent, the method comprising
    incubating the sample with a cyclodextrin polymer resin polymerized to form a resin bead under conditions sufficient to separate at least 95% to 99% of the detergent from the sample and recover at least 84% to 99% of the protein from the sample, wherein the cyclodextrin polymer resin is (2-hydroxyethyl)-β-cyclodextrin (HEBC).

2. The method of claim 1 where separation is by a spin column.

3. The method of claim 1 where separation is by gravity flow.

4. The method of claim 1 where separation is by a batch process.

5. The method of claim 1 where the protein is post-translationally modified.

6. The method of claim 1 where the sample contains a plurality of proteins.

7. The method of claim 1 where the sample contains a protein trypsin digest.

8. The method of claim 1 where the volume of sample to the volume of resin ranges between about 1:1 to about 1:10.

9. A method to prepare a biological sample for mass spectroscopy analysis, the sample containing at least one protein and at least one detergent, the method comprising incubating the sample with a (2-hydroxyethyl)-β-cyclodextrin (HEBC) under conditions sufficient to separate at least 95% of the detergent from the sample and recover at least 84% of the protein from the sample.

* * * * *